United States Patent [19]
Bonutti et al.

[11] Patent Number: 5,395,303
[45] Date of Patent: Mar. 7, 1995

[54] ORTHOSIS WITH DISTRACTION THROUGH RANGE OF MOTION

[75] Inventors: Peter M. Bonutti, 1303 W. Evergreen Plz., Effingham, Ill. 62401; Gary E. Zitzmann, Newton, Ill.

[73] Assignee: Peter M. Bonutti, Effingham, Ill.

[21] Appl. No.: 126,081

[22] Filed: Sep. 23, 1993

Related U.S. Application Data

[60] Division of Ser. No. 690,845, Apr. 24, 1991, Pat. No. 5,285,773, which is a continuation-in-part of Ser. No. 686,811, Apr. 17, 1991, Pat. No. 5,213,094, and a continuation-in-part of Ser. No. 559,770, Jul. 30, 1990, Pat. No. 5,167,612.

[51] Int. Cl.$^6$ .............................................. A61F 5/00
[52] U.S. Cl. ...................................... 602/16; 602/20; 602/23; 602/37; 601/33
[58] Field of Search ............... 602/16, 20, 23, 36, 602/37; 601/23, 33, 34, 40

[56] References Cited

U.S. PATENT DOCUMENTS

| | | |
|---|---|---|
| 3,814,419 | 6/1974 | Bjorklund et al. |
| 3,976,057 | 8/1976 | Barclay |
| 4,039,183 | 8/1977 | Sakurada |
| 4,180,870 | 1/1980 | Radulovic et al. |
| 4,214,577 | 7/1980 | Hoy |
| 4,229,001 | 10/1980 | Roman |
| 4,237,873 | 12/1980 | Terry et al. |
| 4,273,113 | 6/1991 | Hofstein |
| 4,441,489 | 4/1984 | Evans et al. |
| 4,456,001 | 6/1984 | Barber et al. |
| 4,502,681 | 3/1985 | Blomqvist |
| 4,508,111 | 4/1985 | Hepburn |
| 4,509,509 | 4/1985 | Bouvet et al. |
| 4,538,595 | 9/1985 | Hajianpour |
| 4,538,600 | 9/1985 | Hepburn |
| 4,606,542 | 8/1986 | Segal |
| 4,612,919 | 9/1986 | Best |
| 4,665,905 | 5/1987 | Brown |
| 4,718,665 | 1/1988 | Airy et al. |
| 4,790,301 | 12/1988 | Silfverskiold |
| 4,844,454 | 7/1989 | Rogers |
| 4,848,326 | 7/1989 | Lonardo |
| 4,930,497 | 6/1990 | Saringer |
| 4,953,543 | 9/1990 | Grim et al. ........................ 602/16 |
| 4,955,369 | 9/1990 | Bledsoe et al. |
| 5,018,514 | 5/1991 | Grood et al. ........................ 602/16 |
| 5,025,782 | 6/1991 | Salerno |
| 5,027,688 | 7/1991 | Suzuki et al. ................... 602/16 X |
| 5,036,837 | 8/1991 | Mitchell et al. |
| 5,102,411 | 4/1992 | Hotchkiss et al. |
| 5,232,435 | 8/1993 | Leibinsohn .................... 602/20 X |

FOREIGN PATENT DOCUMENTS

| | | |
|---|---|---|
| 0181688 | 5/1986 | European Pat. Off. |
| 0380060 | 8/1990 | European Pat. Off. |
| 2829562 | 7/1978 | Germany |
| 8806231 U | 5/1988 | Germany |
| 1426580A | 9/1988 | U.S.S.R. |
| WO8804543 | 6/1988 | WIPO |

OTHER PUBLICATIONS

Publication by Dynasplint Systems, Inc. entitled "Dynasplint LPS (TM) Orthosis-Knee Extension" (Date Unknown; but prior to Aug. 23, 1991).

Primary Examiner—Richard J. Apley
Assistant Examiner—Linda C. M. Dvorak
Attorney, Agent, or Firm—Tarolli, Sundheim & Covell

[57] ABSTRACT

An orthosis for stretching tissue that limits compressive forces on the soft tissue around a joint during movement of the joint. The orthosis includes two relatively pivotable cuff arms with a cuff on each arm. The cuffs clamp onto the body portions on either side of the joint. The pivot axis of the cuff arms is spaced from the pivot axis of the joint, so that movement of the cuff arms to extend the joint results in distractive forces being applied to the joint. The cuffs are selectively moved on the cuff arms, during extension and flexion, to provide the proper amount of distractive forces to the joint and to limit compressive forces on the joint. A mechanical advantage is gained through the use of a gear drive mechanism for transmitting to the joint the force applied by the patient. This allows the orthosis to be relatively small and light weight. The orthosis also provides a portable system for continuous passive motion therapy for a joint. The orthosis may be operated by a manual plus electric drive cycling it between extremes of motion. Provision is made for monitoring the range of motion or the force applied.

87 Claims, 10 Drawing Sheets

ORTHOSIS WITH DISTRACTION THROUGH RANGE OF MOTION

RELATED APPLICATION

This is a divisional of application Ser. No. 07/690,845, filed, Apr. 24, 1991, (now U.S. Pat. No. 5,285,773). The aforementioned application Serial No. 07/690,845 is itself a continuation-in-part of application Ser. No. 07/559,770, filed Jul. 30, 1990, (now U.S. Pat. No. 5,167,612). The aforementioned application Ser. No. 07/690,845 is also a continuation-in-part of application Ser. No. 07/686,811, filed Apr. 17, 1991, (now U.S. Pat. No. 5,213,094). The benefit of the earlier filing dates of the aforementioned application Ser. No. 7/690,845, 07/559,700 and 07/686,811 has been and hereby is claimed for all common subject matter.

BACKGROUND OF THE INVENTION

Technical Field

The present invention relates to an orthosis for stretching tissue in the human body to regain joint motion and eliminate tissue contracture. In particular, the present invention relates to an orthosis which limits compressive forces on the soft tissue around a joint while it stretches tissue around a joint. The present invention also relates to a continuous passive motion system for joint therapy.

Description of the Prior Art

When the full range of movement of a joint is not available, such as after surgery or trauma, tissue around the joint stiffens and loses its ability to move through the extremes of motion. Various devices have been designed to regain range of motion.

U.S. Pat. No. 4,612,919 shows an adjustable limb support for adjustably orienting the forearm and upper arm of a human patient in a variety of angular relationships to therapeutically treat the contracted muscles in the patient's arm.

U.S. Pat. No. 4,848,326 shows a knee contracture correction device for straightening a contracted knee.

U.S. Pat. No. 4,538,600 shows an adjustable splint assembly with a lower strut and an upper strut pivotably connected to the lower strut. An internal spring applies a force at the pivot point to align the upper and lower struts to straighten the limb to which the splint is attached. A similar device is also shown in U.S. Pat. No. 4,508,111. Similar devices are in use and are sold under the trademark DYNASPLINT by Dynasplint Systems, Inc.

U.S. Pat. No. 4,665,905 shows a dynamic elbow and knee extension device with a centrally positioned compression spring.

It is also known in the art to put a rigid element including a turnbuckle, on the inside angle of a joint, between two cuffs attached to limb segments and use the turnbuckle to vary the length of the rigid element to pull and push the limb segments relative to each other. It has been found that this device does not work very well in practice because it is cumbersome and difficult to obtain relatively full extension or flexion at the extremes of motion.

Each of the above-identified prior art devices, and each of the devices in use at the present time, does not apply adequate force in the appropriate planes. Further, each of these devices applies undesirable compressive forces on the soft tissues around a joint upon flexion and extension of the joint. None allows the patient to provide the proper therapy by himself, without the assistance of a therapist who manually stretches the joint. None allows the patient to control the therapy process in a self-directed manner.

Accordingly, it is desirable to provide a self-directed therapy device which not only enhances the range of motion of the joint but also limits compressive joint forces, distracts the joint and stretches soft tissue. "Distraction" is defined by one dictionary as "Separation of the surfaces of a joint by extension without injury or dislocation of the parts." (*Taber's Cyclopedic Medical Dictionary*, 16th Edition, 1989, page 521), and involves stretching rather than compressing the joint capsule, soft tissue, ligaments, and tendons.

The device should limit tissue damage by controlling the amount of force applied, and should apply a progressive gradual stretching action and have a locking mechanism to maintain a joint in a selected position, because tissue is viscoelastic. This is the best way to establish or reestablish a range of motion in the soft tissues around a joint, as it does not involve damaging the tissue.

An orthosis should also be lightweight and portable so that it can be used in a seated, upright, or functional position. This should be the case for both a stretching device and a continuous passive motion (CPM) device.

SUMMARY OF THE INVENTION

In the earlier filed co-pending applications identified above, there were disclosed orthoses having certain novel features and advantages. The present invention is an improved version of the earlier orthoses.

As in the earlier orthoses, a tower provides mechanical advantage for increasing the range of motion of the joint. A significant mechanical advantage is also gained through the use of a gear drive mechanism for transmitting to the joint the force applied by the patient. This allows the orthosis to be relatively small and light weight. This mechanical advantage can also be achieved through the use of drive mechanisms other than the gear drive. In any case, the drive mechanism can deliver appropriate force or greater force to stretch soft tissue.

In the present invention, the orthosis provides for distraction of the joint through the entire range of motion. The orthosis includes two relatively pivotable cuff arms. Each cuff arm has a cuff mounted on the cuff arm. The cuffs clamp onto the body portions on either side of the joint. The pivot axis of the cuff arms is spaced from the pivot axis of the joint. Movement of the cuff arms to extend the joint results in distractive forces being applied to the joint. These distractive forces are limited and controlled by having the cuffs slidable on the cuff arms. The cuffs are selectively moved along the cuff arms, during relative movement of the cuff arms, to provide the proper amount of distractive forces to the joint and to limit compressive forces on the joint. Thus, the orthosis is well suited for stretching therapy.

The orthosis may also provides an optional system for continuous passive motion therapy for a joint. The orthosis is light weight and may be operated by an electric motor cycling it between flexion and extension. This may also be done in combination with the manual stretching therapy.

BRIEF DESCRIPTION OF THE DRAWINGS

The foregoing and other features of the present invention will become apparent to one skilled in the art upon a consideration of the following description of the invention with reference to the accompanying drawings, wherein.

DESCRIPTION OF PREFERRED EMBODIMENTS OF THE INVENTION

Figure 1:
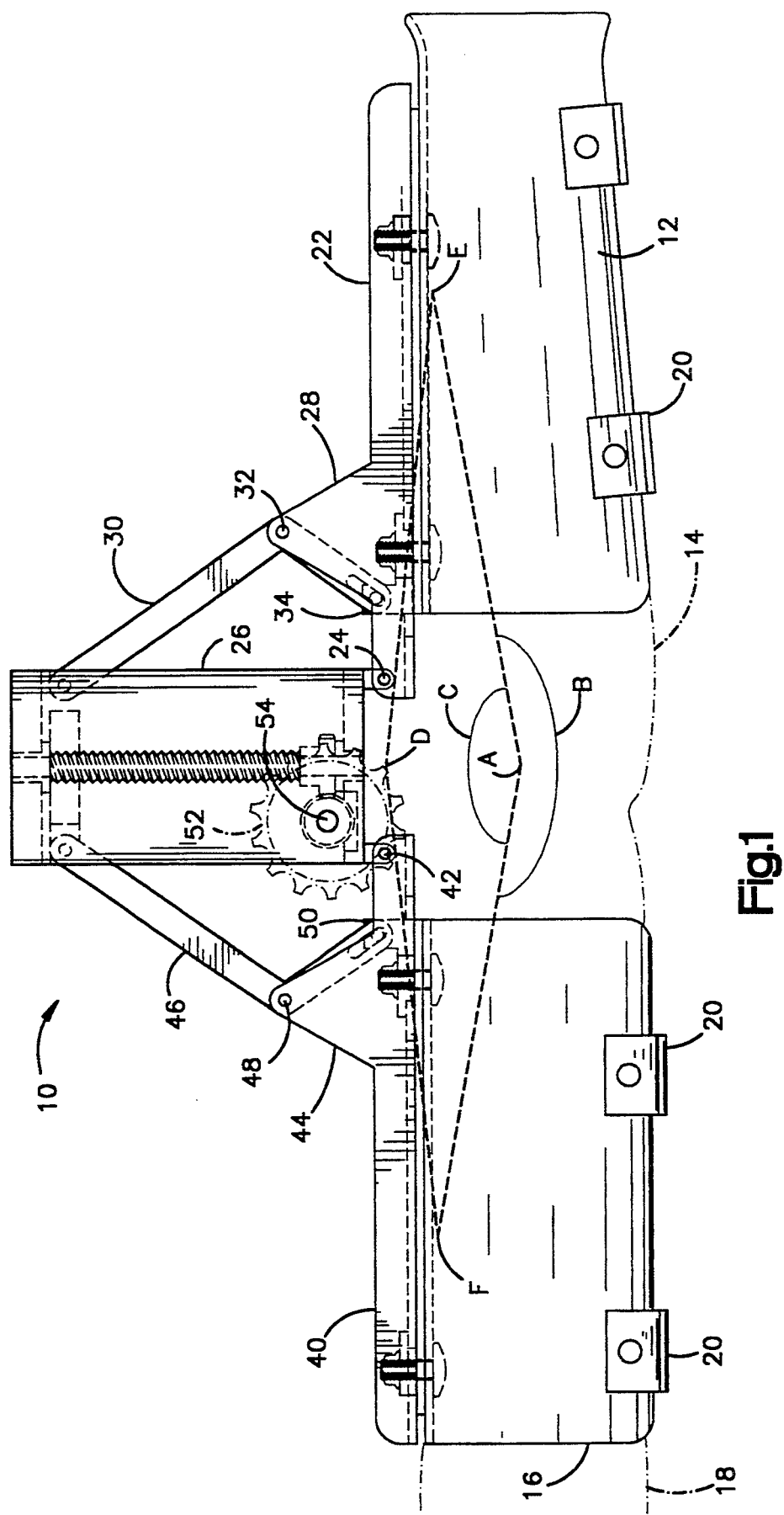
FIG. 1 is a view of an orthosis in accordance with the present invention.

The present invention relates to an orthosis and particularly to an orthosis for moving a joint between first and second relatively movable body portions. The present invention is applicable to various orthosis constructions. As representative of the present invention, FIG. 1 illustrates generally an orthosis 10. In FIG. 1 the orthosis 10 is illustrated as attached to a human arm, for moving the elbow joint which is between the upper arm and the forearm.

It should be understood that the orthosis 10 can be used to extend or flex other joints in the body, such as a knee joint or a wrist joint or ankle joint, with the construction of the orthosis 10 in such case being varied to fit the particular application. The orthosis can be used, for example, to flex the ankle joint to stretch a tight achilles tendon in cerebral palsy or post traumatic contractures. It is especially useful in obtaining the last degrees of joint extension. The orthosis can be custom made to fit a particular individual, or can be an off the shelf item. The orthosis can also be used, for example, to eliminate contractures or stress soft tissue. It can be used for patients with cerebral palsy, stroke, spastic paralysis, as well as in post-traumatic or post-surgical cases. It can also be used, for example, in therapy after a knee replacement, in which the extremes of motion in extension or flexion are difficult to obtain without extensive intervention of a therapist.

The orthosis 10 includes a first cuff 12 for attachment to a first body portion 14 such as the forearm, and a second cuff 16 for attachment to a second body portion 18 such as the upper arm. (The term "cuff" as used herein means any suitable structure for transmitting the force of the orthosis to the limb portion it engages.) The first body portion 14 is joined to the second body portion 18 at the elbow joint designated A, around which is located, as is well known, soft tissue. Each of the first and second cuffs 12 and 16 includes a plurality of loop connectors 20 for receiving straps extending around the body portions 14 and 18 to clamp the cuffs 12 and 16 to the body portions 14 and 18.

The first cuff 12 is mounted for sliding movement on a first cuff arm 22. (The term "cuff arm" as used herein means any suitable structure for transmitting the force of the orthosis to the cuff and thence to the limb portion.) The first cuff arm 22 is pivotally mounted by a pin 24 to a tower 26. The first cuff arm 22 includes a support 28. A first lever arm 30 extends from the tower 26 and is pivotally connected to the support 28 by a pin 32. The first lever arm 30 is pivotally connected to a cuff actuator block 34. The cuff actuator block 34 is fixed to the first cuff 12 and is slidable along the first cuff arm 22 in a manner as described below.

The second cuff 16 is mounted for sliding movement on a second cuff arm 40. The second cuff arm 40 is pivotally mounted by a pin 42 to the tower 26. The second cuff arm 40 includes a support 44. A second lever arm 46 extends from the tower 26 and is pivotally connected to the support 44 by a pin 48. The second lever arm 46 is pivotally connected to a cuff actuator block 50. The cuff actuator block 50 is fixed to the second cuff 16 and is slidable along the second cuff arm 40 in a manner as described below.

The tower 26 is a box-like structure including a lower housing 66 and an upper housing 70 joined by a front plate 51 and a back plate 53. A drive mechanism for the orthosis 10 is disposed substantially within the tower 26. The drive mechanism includes a manually actuatable knob 52 (FIG. 1) which is fixed to a shaft 54. The shaft 54 extends halo the tower 26 and a gear 56 (FIG. 2) is fixed to the shaft. The gear 56 engages external gear teeth 58 on a gear 60. Rotation of the gear 56 about its axis causes rotation of the gear 60 about its axis.

The gear 60 is fixed to an externally threaded lead screw 62. One end of the lead screw 62 is journalled for rotation in a bushing 64 mounted in a lower housing 66 of the tower 26. The opposite end of the lead screw 62 is journalled for rotation in a bushing 68 mounted in an upper housing 70 of the tower 26. An arm actuator block or base link 72 has an internally threaded opening 74 though which the lead screw 62 extends in threaded engagement. As the lead screw 62 rotates, the actuator block moves axially along the lead screw 62 within the tower 26.

A pin 76 is fixed in the arm actuator block 72. The pin 76 extends through an opening 78 in a first portion 80 of the first lever arm 30. The first lever arm 30 is L-shaped, having an elbow portion 82 intermediate the first portion 80 and a second portion 84. An opening 86 extends though the elbow portion 82 of the first lever arm 30. A pin 88 fixed in the support 28 of the first cuff arm 22 extends through the opening 86. A slot 90 extends through the second portion 84 of the first lever arm 30.

Figure 4:
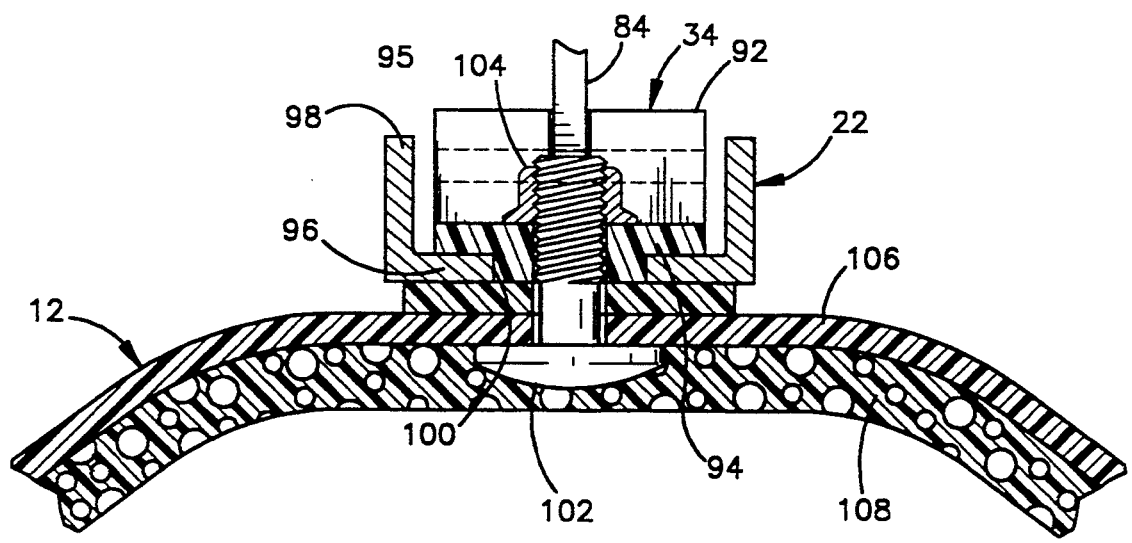
FIG. 4 is a sectional view through a cuff attachment point including the cuff actuator block.

The cuff actuator block 34 (FIG. 4) includes a pin portion 92 and a guide portion 94. The pin portion 92 has an open center and receives therein the slotted second portion 84 of the first lever arm 30. A pin 95 having its ends fixed in the pin portion 92 extends through the slot 90 in the lever arm portion 84, thus connecting the first lever arm 30 to the cuff actuator block 34.

Each cuff arm functions as a track along which its respective cuff slides. Each cuff arm may thus take any suitable shape. In a preferred embodiment, the cuff arms are U-shaped and include a bottom portion and upstanding side portions. Thus, the first cuff arm 22 is U-shaped and includes a bottom portion 96 and a side portion 98. Part of the guide portion 94 of the cuff actuator block 34 is supported on the bottom portion 96 of the first cuff arm 22. Part of the guide portion 94 is received in a slot 100 in the first cuff arm 22.

A bolt 102 extends through the slot 100 and with a nut 104 secures the cuff actuator block 34 to the shell 106 of the first cuff 12. The nut 104 is turned down only tightly enough to secure the cuff actuator block 34 for movement with the cuff shell 106, while allowing the shell 106 to slide relative to the first cuff arm 22. The head of the bolt 102 is within a layer 108 of padding on the inside of the shell 106.

Figure 3:
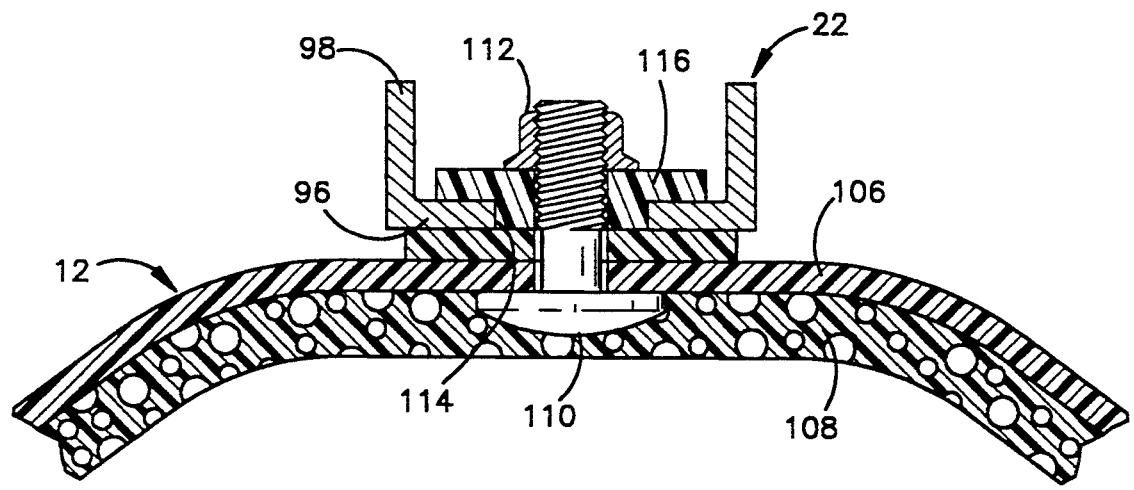
FIG. 3 is a sectional view through a cuff attachment point.

The first cuff 12 is also slidably mounted to the first cuff arm 22 at a second location (FIGS. 3 and 5) by a bolt 110 and a nut 112. The bolt 110 extends through a slot 114 in the bottom portion of the first cuff arm 22 and through a beating 116 which mounts the first cuff 12 for sliding movement relative to the first cuff arm 22. Again, the nut 112 is turned down only tightly enough to secure the bearing 116 for sliding movement with the shell 106, while allowing the shell 106 to slide relative to the first cuff arm 22.

The second cuff 16 is similar to the first cuff 12, differing in the illustrated embodiment only in that it is shorter to fit the second body portion 16 rather than the first body portion 14. Similarly, the second cuff arm 40 is similar to the first cuff arm 22, differing in the illustrated embodiment only in that it is shorter to fit the shorter second cuff 16. It should be understood that the cuffs are, in any particular embodiment, sized to fit the particular body portion (leg, arm, ankle, etc.) to which they are to be connected. Accordingly, the illustration of the second cuff being shorter than the first cuff is only in one particular application and is not to be considered limiting in any regard. All the other parts of the drive mechanism, etc. are similar between the two sides of the orthosis.

In accordance with a feature of the present invention, the pivot point of the cuff arms 22 and 40 is spaced outwardly from the joint A, so that the joint A can be distracted. The first body portion 14, the joint A, and the second body portion 16 define on one side of the joint A an inner sector "B" (inside the bend of the limb) which decreases in angle as the joint A is flexed (bent). The first body portion 14, the joint A, and the second body portion 16 define on the opposite side of the joint A an outer sector "C" which decreases in angle as the joint A is extended (straightened). The tower 26 is located in the outer sector "C".

The pivot axis of the cuff arms is represented by the point D in the outer sector C (see FIG. 1). The distance between the point D and a point E on the first cuff arm 22 is the same as the distance between the point D and a point F on the second cuff arm 40. The dotted line triangles in FIG. 1 illustrate the relative positions of the various points in FIG. 1.

Assuming that the first body portion 14 were securely fixed to the first cuff arm 22 by the first cuff 11, and that the second body portion 18 were securely fixed to the second cuff arm 40 by the second cuff 16, then upon rotation of the cuff arms relative to each other from a more flexed position to a more extended position, the points E and F would move upwardly as viewed in FIG. 1. Since the distance between the points A and D would not change, then the joint A would be subjected to distractive forces tending to pull the joint A apart.

It can thus be seen that, because the pivot point D of the cuff arms 22 and 40 is spaced outwardly from the joint A, when the orthosis 10 is extended, the joint A is distracted. Thus, the tower 26 provides a triangular or tripod effect and also serves to provide an increased moment arm for the first and second lever arms 30 and 46.

Such distraction of the joint is desirable, as noted above. However, it has been found an excessive amount of distractive force can be applied in this manner. Accordingly, in the orthosis 10 according to the present invention, the amount of distraction is controlled in a manner described below.

Extension

In operation of the orthosis illustrated in FIGS. 1-5, the knob 52 is rotated by the application of an external force. The knob 52 is fixed to the shaft 54 and the gear 56, and thus the gear 56 rotates. The gear 56 causes the gear 60 to rotate. The gear 60 is fixed to the lead screw 62, and thus the lead screw 62 rotates. Rotation of the lead screw 62 results in axial movement of the arm actuator block 72. The gearing provides a substantial mechanical advantage in the operation of the drive mechanism. The gear ratios may be selected to give the desired amount of cuff arm movement for a given amount of force input to the orthosis.

Figure 5:
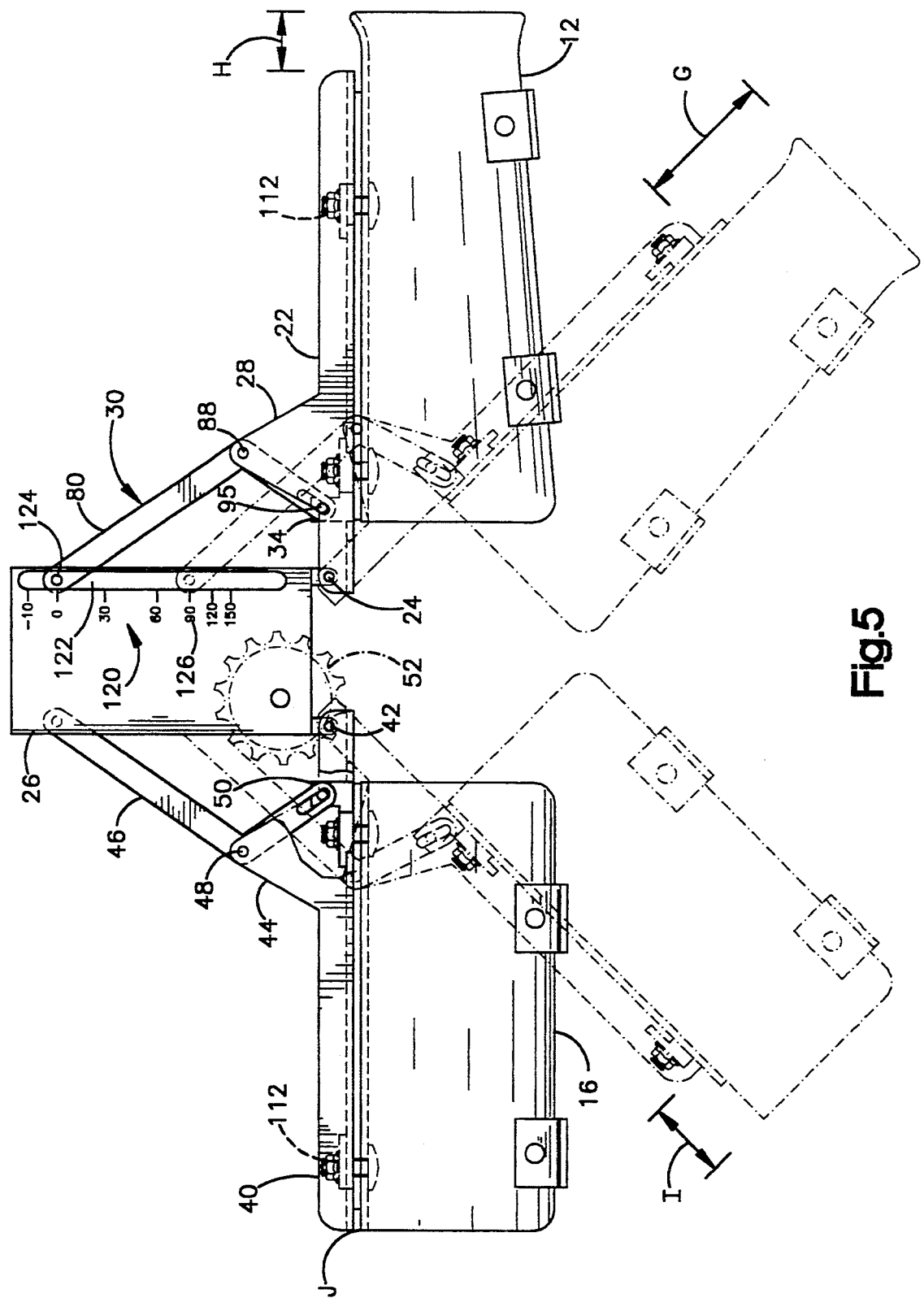
FIG. 5 is a view showing the orthosis of FIG. 1 in two positions of its range of motion.

In operation of the orthosis 10 to extend the joint, the orthosis 10 starts at a more flexed position such as the position shown in dashed lines in FIG. 5. The first and second cuffs 12 and 16 are clamped onto the first and second body portions 14 and 18 (FIG. 1), respectively, by straps through the loops 20, tightly enough so that the cuffs 12 and 16 can apply torque to the body portions 14 and 18 to extend the joint A.

Figure 2:
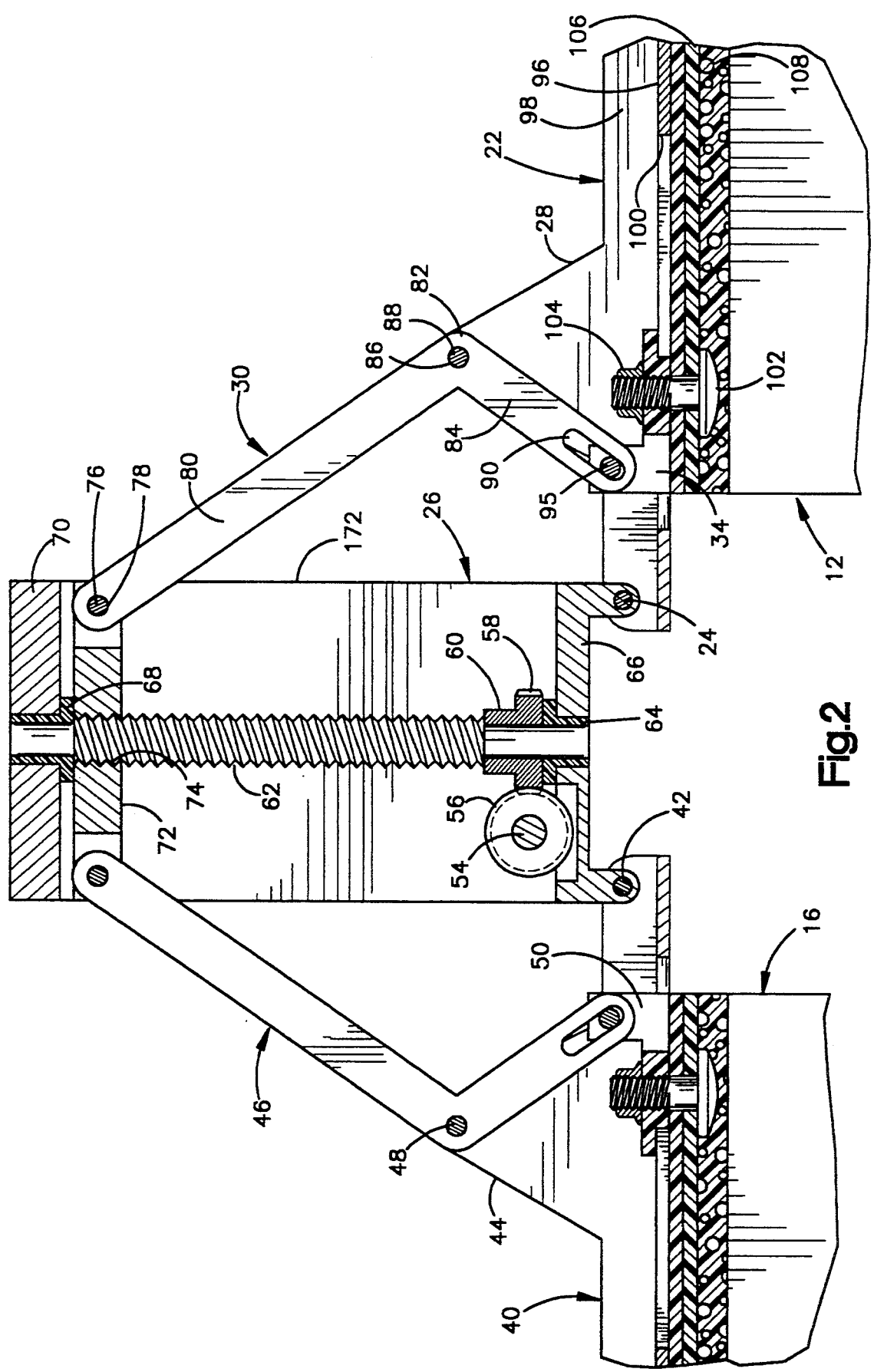
FIG. 2 is an enlarged sectional view of a portion of the orthosis of FIG. 1 including the drive mechanism.

The knob 52 is turned so that the arm actuator block 72 moves upward as viewed in FIGS. 2 and 5, that is, toward the upper housing 66. As the arm actuator block 72 moves upward, it moves the pin 76 upward also. The pin 76 applies an upwardly-directed force on the first portion 80 of the first lever arm 30. This force is transmitted to and through the pin 88, the support 28, and to the first cuff arm 22. The first cuff arm 22 pivots about the pin 24, toward the position shown in solid lines in FIG. 2.

The first lever arm 30 also applies an upwardly-directed force on the pin 95 fixed to the cuff actuator block 34. As the first cuff arm 22 pivots relative to the tower 26, the cuff actuator block 34, because it can slide along the first cuff arm 22, moves inwardly along the first cuff arm 22. The first cuff 12, which is fixed to the cuff actuator block 34, also moves inwardly along the first cuff arm 22. This can be seen clearly in FIG. 5 by comparing the distance marked G, to the distance marked H. The distance marked G is the distance between the end of the first cuff 12 and the end of the first cuff town 22 when the orthosis is in a relatively flexed condition. The distance marked H is the distance between the end of the first cuff 12 and the end of the first cuff arm 22 when the orthosis is in a relatively extended condition. The distance marked G is greater than the distance marked H.

The operation with respect to the second cuff arm 40 is similar. As the arm actuator block 72 moves upward, it applies an upwardly-directed force on the second lever arm 46. This force is transmitted to and through the support 44 to the second cuff arm 40. The second cuff arm 40 pivots about the pin 42, toward the position shown in solid lines in FIG. 2.

The second lever arm 46 also applies an upwardly-directed force on the cuff actuator block 50. As the second cuff arm 40 pivots relative to the tower 26, the cuff actuator block 50, because it can slide along the second cuff arm 40, moves inwardly along the second cuff arm 40. The second cuff 16, which is fixed to the cuff actuator block 50, also moves inwardly along the cuff arm 40. This can be seen clearly in FIG. 5 by comparing the distance marked I to the distance marked J. The distance marked I is the distance between the end of the second cuff 16 and the end of the second cuff arm 40 when the orthosis is in a relatively flexed condition. The distance marked J is the distance between the end of the second cuff 16 and the end of the second cuff arm 40 when the orthosis is in a relatively extended condition. The distance marked I is greater than the distance marked J.

Because the cuffs are clamped onto the first and second body portions as described above, the outward pivoting movement of the cuff arms and the cuffs causes the joint to be extended as desired. However, this extension of the joint, as described above, can place strong distractive forces on the soft tissues around the joint. The sliding movement of the cuffs, inwardly along the cuff arms, helps to limit these distractive forces by counteracting the outward movement of the cuff arms. Preferably, the cuffs slide inwardly along the cuff arms a distance far enough so that the joint is only slightly distracted during extension. Thus, the detrimental effects of strong distractive forces normally generated in forced extension of a joint are avoided, being replaced with the beneficial effects of limited and controlled distraction.

Flexion

In operation of the orthosis 10 to flex a joint, the orthosis 10 starts at a more extended position such as the position shown in solid lines in FIG. 5. The first and second cuffs 12 and 16 are clamped onto the first and second body portions 14 and 18 (FIG. 1), respectively, by straps through the loops 20, tightly enough so that the cuffs 12 and 16 can apply torque to the body portions 14 and 18 to extend the joint A.

The knob 52 is turned so that the arm actuator block 72 moves downward as viewed in FIGS. 2 and 5, that is, toward the lower housing. As the arm actuator block 72 moves downward, it applies a downwardly-directed force on the first portion 80 of the first lever arm 30.

This force is transmitted to and through the pin 88, the support 28, and to the first cuff arm 22. The first cuff arm 22 pivots about the pin 24, toward the position shown in dashed lines in FIG. 5.

The first lever arm 30 also applies a downwardly-directed force on the pin 95 fixed to the cuff actuator block 34. As the first cuff arm 22 pivots relative to the tower 26, the cuff actuator block 34, because it can slide along the first cuff arm 22, moves outwardly along the first cuff arm 22. The first cuff 12, which is fixed to the cuff actuator block 34, also moves outwardly along the first cuff arm 22. This can be seen clearly in FIG. 5 by comparing the distance marked G, to the distance marked H. The distance marked G is the distance between the end of the first cuff 12 and the end of the first cuff arm 22 when the orthosis is in a relatively flexed condition. The distance marked H is the distance between the end of the first cuff 12 and the end of the first cuff arm 22 when the orthosis is in a relatively extended condition. The distance marked G is greater than the distance marked H.

The operation with respect to the second cuff arm 40 is similar. As the arm actuator block 72 moves downward, it applies a downwardly-directed force on the second lever arm 46. This force is transmitted to the second cuff arm 40. The second cuff arm 40 pivots about the pin 42 relative to the tower 26, toward the position shown in dashed lines in FIG. 2.

The second lever arm 46 also applies a downwardly-directed force on the cuff actuator block 50. As the second cuff arm 40 pivots relative to the tower 26, the cuff actuator block 50, because it can slide along the second cuff arm 40, moves outwardly along the second cuff arm 40. The second cuff 16, which is fixed to the cuff actuator block 50, also moves outwardly along the second cuff arm 40. This can be seen clearly in FIG. 5 by comparing the distance marked I to the distance marked 3. The distance marked I is the distance between the end of the second cuff 16 and the end of the second cuff arm 40 when the orthosis is in a relatively flexed condition. The distance marked J is the distance between the end of the second cuff 16 and the end of the second cuff arm 40 when the orthosis is in a relatively extended condition. The distance marked I is greater than the distance marked J.

Because the cuffs are clamped onto the first and second body portions as described above, the inward pivoting movement of the cuff arms and thus the cuffs causes the joint to be flexed as desired. However, this flexion of the joint can place strong compressive forces on the soft tissues around the joint. The sliding movement of the cuffs, outwardly along the cuff arms, helps to limit these compressive forces by counteracting the inward movement of the cuff arms. Preferably, the cuffs slide outwardly along the cuff arms a distance far enough so that the joint is actually distracted somewhat during flexion. Thus, the detrimental effects of the compressive forces normally generated in forced flexion of a joint are avoided, being replaced with the beneficial effects of a controlled amount of distraction.

The orthosis in accordance with the present invention may include means for monitoring the angle between the first and second cuff arms 22 and 40. In one embodiment, this may be a goniometer 120 as illustrated in FIG. 5. A slot 122 extends along the length of the tower 26. A pin 124 on the first lever arm 30 is visible through the slot 122. The position of the pin 124 is readable against a scale 126 indicating degrees of flexion of the joint. As the first and second lever arms 30 and 46 pivot relative to each other, the first lever arm 30 moves downward in the tower 126. The pin 124 moves along the slot 122 and indicates the relative position of the two cuff arms 22 and 40. Equivalent manners of measuring the angle between the two arms are possible and are included within the scope of the invention.

An orthosis in accordance with the present invention may include means for adjusting the angle between a cuff arm and the cuff attached thereto. This can be used to apply an initial biasing force in one direction, or to position the limb portion initially within the cuff. This can also be used to accommodate angular displacement between the first and second body portions. For example, in an elbow joint there is normally about a 7° angle between the upper arm and the forearm.

Figure 7:
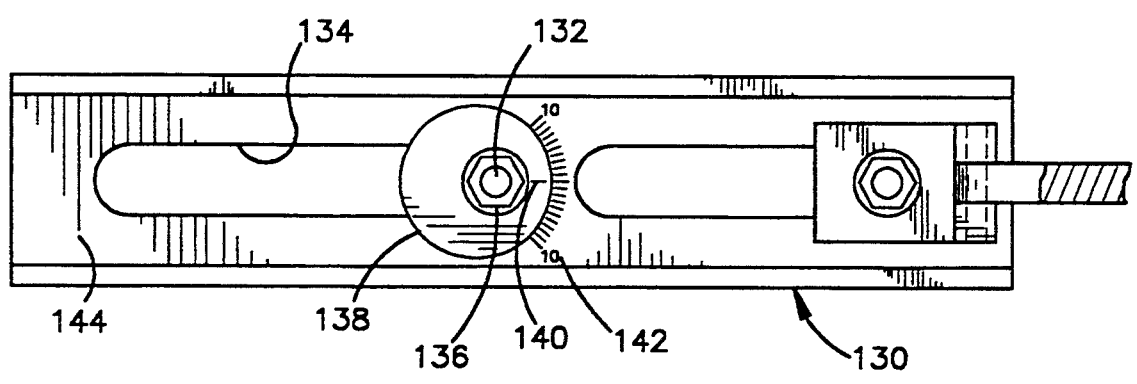
FIG. 7 is a view of a structure for varying angular attachment of the cuffs to the cuff arms.

In one embodiment, this may be a mechanism as illustrated in FIG. 7, which is a top plan view of a portion of a cuff arm 130. A cuff attachment screw 132 is movable in a slot 134 and can be slidably fixed in position with a nut 136, as in the embodiment of FIGS. 1–5. However, the opening in the bearing 138 through which the screw 132 extends is off-center of the bearing 138. Also, the bearing 138 has a marker 140 readable against a scale 142 on the bottom portion 144 of the cuff arm 130. Rotation of the bearing 138 in the slot 134 moves the screw 132 off the longitudinal center line of the cuff arm 130. This causes the cuff (not shown in FIG. 7) fixed to the screw 132 to be rotated with respect to the cuff arm 130. The cuff can then be fixed in a given angular orientation relative to the cuff arm 132. Equivalent manners of setting an angular orientation between a cuff and its cuff arm are possible and are included within the scope of the invention.

Figure 6:
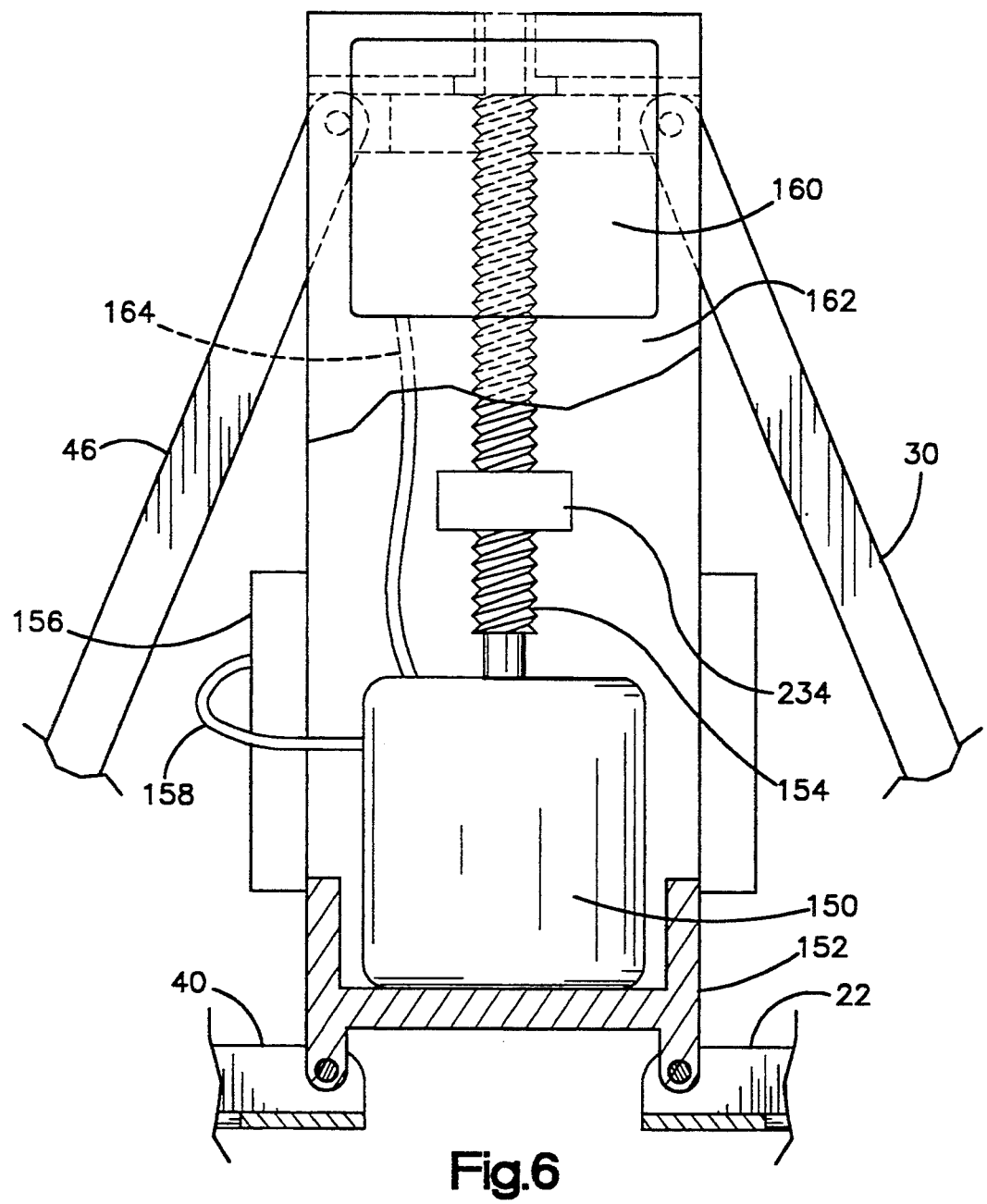
FIG. 6 is a view of an orthosis having an electric motor drive.

The drive mechanism for an orthosis in accordance with the present invention can be actuated by an electric motor instead of by a manually actuatable member such as the knob 52. FIG. 6 illustrates one way of utilizing an electric motor for this purpose.

In FIG. 6, an electric motor 150 is mounted in the lower portion of a tower 152. The motor 150 is drivingly connected to a lead screw 154. The lead screw 154 moves the lever arms 30 and 46 in the same manner as in the embodiment of FIGS. 1–5. The lever arms 30 and 46 move the cuff arms 22 and 40 in the same manner as in the embodiment of FIGS. 1–5.

A battery 156 secured to the back plate of the tower 152 provides electric power to the motor 150 through wires 158. Alternatively, the motor could be supplied with external power. A microprocessor indicated schematically at 160 and mounted on the front plate 162 of the tower 152 controls the operation of the motor 150 through signals sent along wires 164. The microprocessor 160 and motor 150 together can be used to cycle the cuff arms 22 and 40 through extension and flexion; to move the cuff arms 22 and 40 in one pivotal direction a certain amount, hold there while tissue stretches, then move further in that direction; or in any other manner. In another manner of use, the orthosis can be set to cycle to one end of the joint's range of motion and hold there for a predetermined period of time, then cycle to the other end of the joint's range of motion and hold there. The programming and control of the microprocessor 160 is within the skill of the art as it relates to driving the motor to control the cuff arms 22 and 40 to move in known manners. This embodiment is ideally suited for continuous passive motion exercise, because the orthosis is portable and because the motor can be programmed with the desired sequence of movements.

It should be understood that the particular physical arrangement of the motor 150, the battery 156, and the microprocessor 160, which is illustrated and described herein, is not the only possible arrangement of those elements. The invention contemplates that other arrangements of these or similarly functional elements are quite suitable, and thus, the invention is intended to cover any such arrangement.

Figure 9:
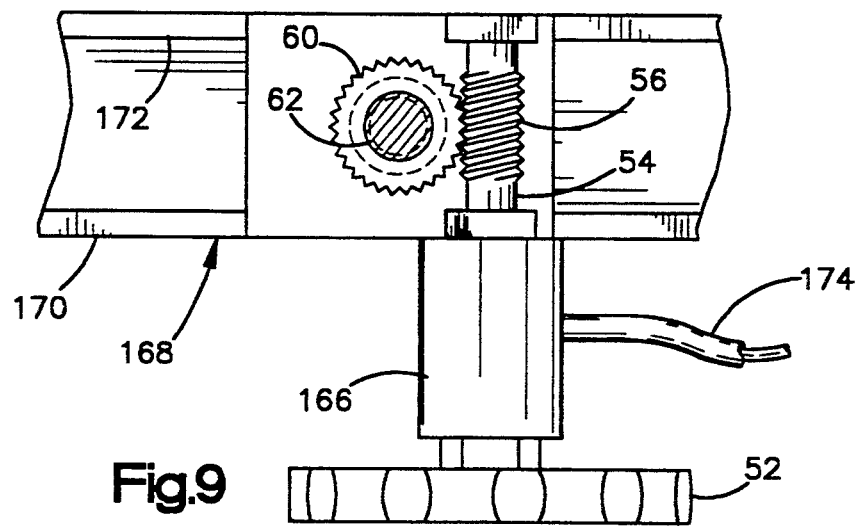
FIG. 9 is a plan view of an orthosis having an alternate electric drive, combined with a manual drive.

FIG. 9 illustrates an alternative method of using an electric motor drive. An electric motor 166 is mounted on the outside of a tower 168, on the front plate 170 of the tower 168. The motor 166 drives the shaft 54 which extends between the front plate 170 and the back plate 172 of the tower 168. The shaft 54 carries the gear 56, as in the embodiment of FIGS. 1–5. The motor 166 is supplied with electric power, and control signals, through wires 174. A manually actuatable member such as a knob 52 is also drivingly connected to the shaft 54. When the knob 52 is used to actuate the orthosis manually, the motor 166 freewheels. Thus, the orthosis illustrated in FIG. 9 can be used either manually, or with an electric motor drive, or both. Therefore, the orthosis is ideally suited for both stretching therapy and CPM therapy.

Figure 8:
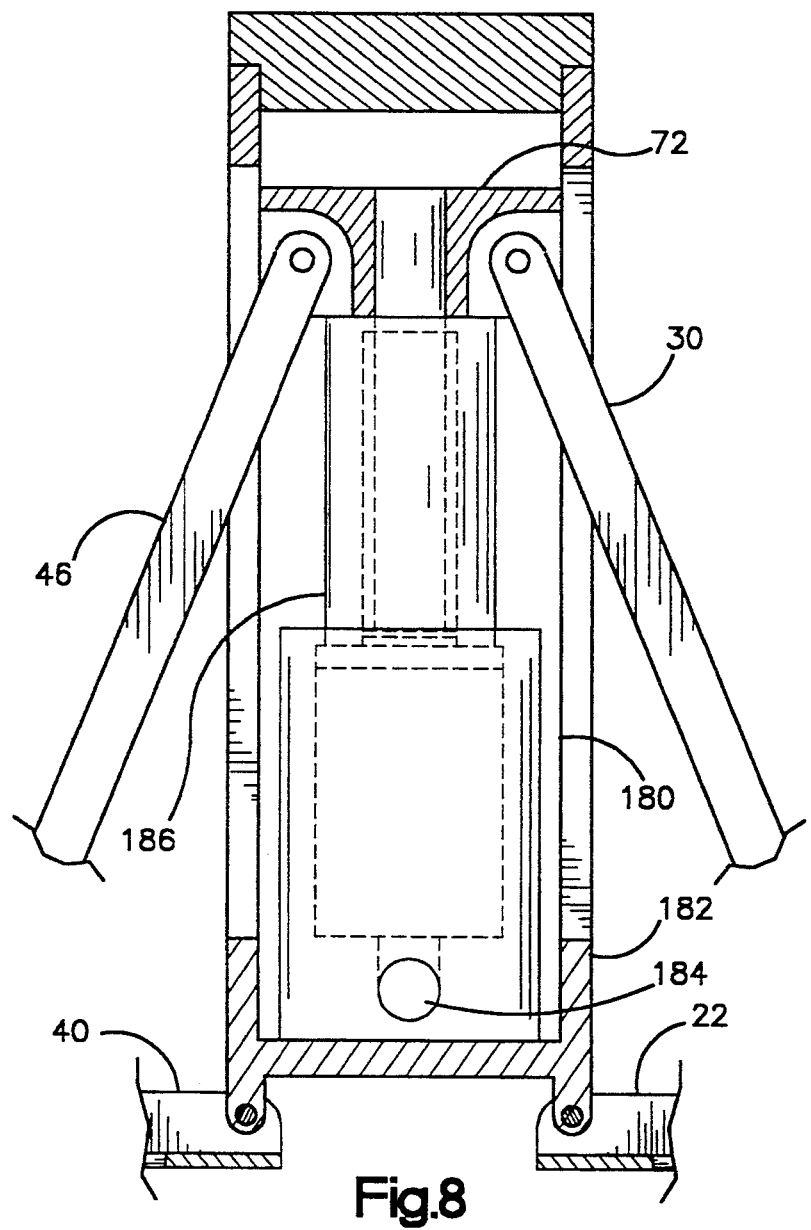
FIG. 8 is a view of an orthosis having a fluid drive.

Another type of power source, other than an electric motor, can also be used. For example, FIG. 8 illustrates the use of a hydraulic or pneumatic motor 180 as the drive mechanism for an orthosis in accordance with the present invention. The motor 180 is fixed in the lower portion of a tower 182. Fluid under pressure is supplied to the motor through a port 184. Actuation of the motor 180 causes a piston 186 to move axially in the tower 182. The piston 186 is connected to the arm actuator block 72. Axial movement of the piston 186 causes axial movement of the am actuator block 72 to drive the lever arms 30 and 46 and the cuff arms 22 and 40 in the same manner as in the embodiment of FIGS. 1–5. Thus, it can be seen that many different types of power sources are suitable for use with an orthosis in accordance with the present invention.

An orthosis in accordance with the present invention can also be used to move a joint when one or both of the bone portions around the joint has projecting pins or K-wires. For example, after some types of bone surgery, the surgeon leaves pins or K-wires projecting from the bone through the skin. The fact that the arm is in this condition does not mean that therapy can not be applied. Rather, the pins or K-wires can be utilized to apply, directly to the bone, the force supplied by the orthosis.

Figure 10:
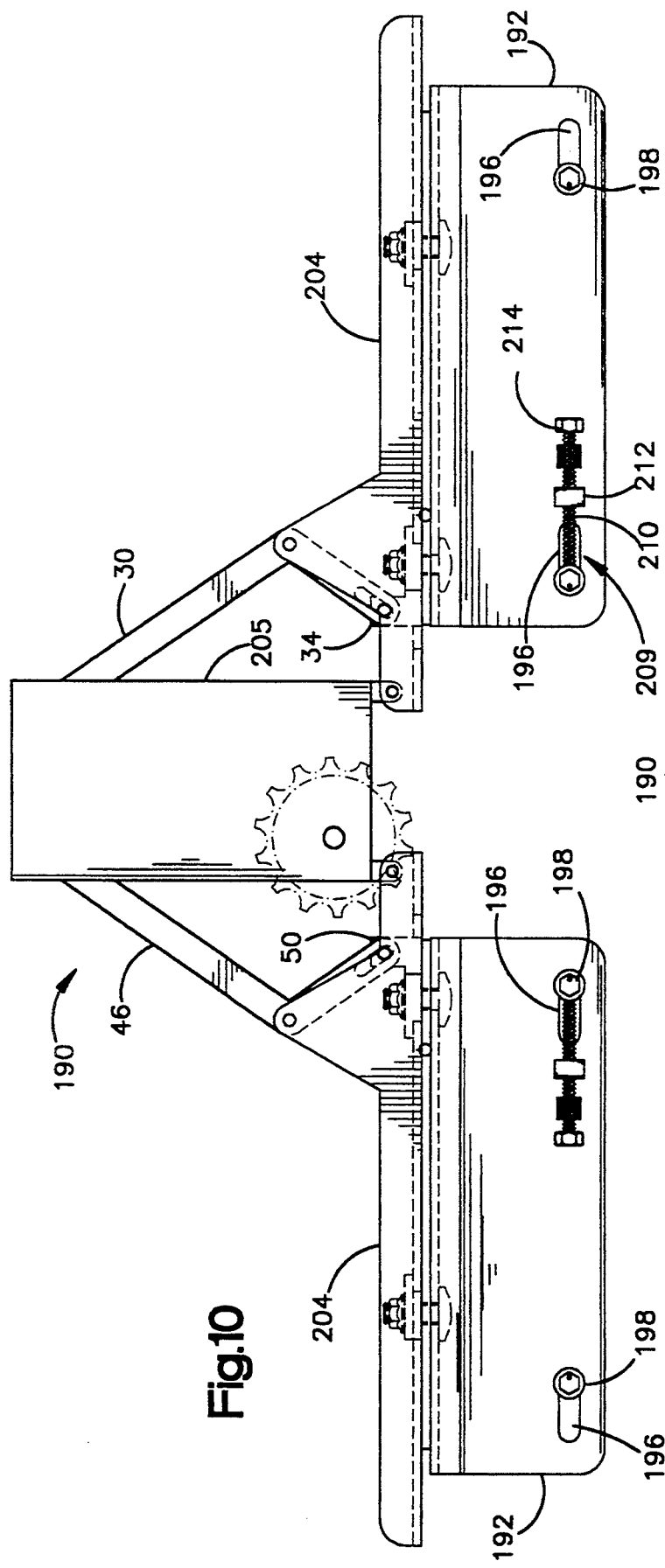
FIG. 10 is a view similar to FIG. 1 of an orthosis having structure for adjusting longitudinal placement of the cuffs relative to the body portions.
Figure 11:
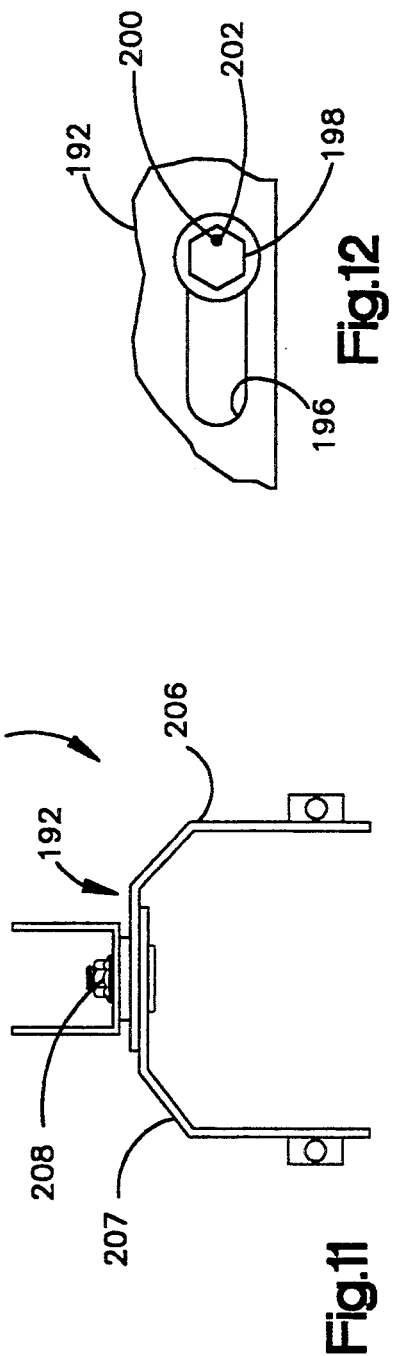
FIG. 11 is an end view of the orthosis of FIG. 10 showing structure for adjusting the width of a cuff.
Figure 12:
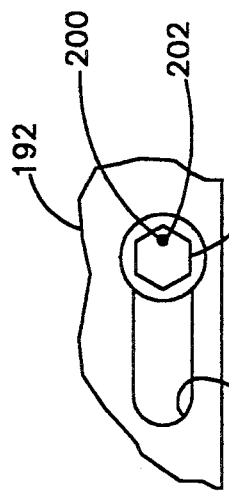
FIG. 12 is an enlarged view of a portion of the orthosis of FIG. 10 showing structure for adjustably receiving a pin or K-wire.

The orthosis 190 illustrated in FIGS. 10–12 is one example. It should be understood that the design of such an orthosis can vary depending on the placement of the pins or k-wires and the therapy to be applied. The design will also vary depending on what particular joint is being moved by the orthosis.

In FIG. 10, the orthosis cuffs 192 each have longitudinally extending slots 196 for receiving cuff attachment screws 198. Each screw has an opening 200 for receiving a pin or K-wire 202. The screw 198 clamps onto the K-wire strongly enough to transmit torque to the bone through the pin or K-wire. As the cuffs slide along the cuff arms 204, and as the arms 204 pivot relative to the tower 205, the body portions to which the cuffs 192 are attached also are moved. Thus, the force of the orthosis is applied directly to bone through the pins or K-wires.

The opening 200 may be eccentrically located in the screw 198 as seen best in FIG. 12. Rotation of the screw 198 relative to the cuff 192 moves the pin 200 relative to the cuff 192. The cuff 192 can then be fixed in a given angular orientation relative to the body portion from which the pin 200 projects. This adjustment can be used to compensate for the particular location of the pins or K-wires, or can be used to apply an initial biasing force in one direction, or to position the limb portion initially within the cuff.

The cuff 192 may include, as best seen in FIG. 11, two cuff side portions 206 and 207 which are slidable relative to each other to position the cuff 192 as well as possible relative to the limb portion. A locking adjuster 208, which may be of a known construction to allow sliding movement then locking in position, is used to position the cuff side portions 206 and 207 relative to each other.

Further, the initial longitudinal positioning of a screw 198 along the cuff 192 can be adjusted using the positioner mechanism 209 shown in FIG. 10. The cuff attachment screw 198 is connected to a screw 210 which extends through a block 212 fixed to the cuff 192. The screw 210 is rotatable by an adjuster 214. Rotation of the screw 210 moves the cuff attachment screw 198 axially relative to the cuff 192. Again, this adjustment can be used to compensate for the particular location of the pins or K-wires, or can be used to apply an initial biasing force in one direction, or to position the limb portion initially within the cuff. It should be noted that this type of positioner mechanism, as well as the two-part cuff illustrated in FIG. 11, can be used in conjunction with orthoses other than the orthosis illustrated in FIGS. 10-12. It should also be noted that, if threaded pins are used in the bone, as is sometimes done, the pins can be threaded directly into nuts on the orthosis.

Another advantage of the gear drive mechanism is that it can provide an automatic locking mechanism for blocking movement of the parts of the orthosis in an undesired direction. Because the mechanism is geared down substantially to provide a mechanical advantage, it is difficult to rotate the gears by moving the cuff arms relative to each other. Therefore, if force is applied to the orthosis to extend a joint slightly against the resistance of the soft tissues of the joint, then the force is released, the orthosis and joint will maintain that extended position, and will not revert to the starting position.

This "locking" ability can also be provided by means of a ratchet drive mechanism. Such a mechanism is indicated schematically in FIG. 14, which shows a ratchet drive mechanism 230 of a known construction disposed in the line of force transmission between the knob 52 and the shaft 54 carrying gear 56. The ratchet drive mechanism 230 is operative to allow rotation of the knob 52 and the shaft 54 in one selected direction of rotation, while blocking rotation of the knob 52 and the shaft 54 in the opposite direction. Thus, the patient can turn the knob 52 in the desired direction to move the joint to which the orthosis is attached from a first position to a second position, then release the knob 52. The ratchet mechanism holds the knob 52 from turning back in the opposite direction, thus holding the joint in the second position.

These locking mechanisms are desirable, to maintain a joint in a selected position, because tissue is viscoelastic. That is, tissue will stretch a certain amount, then if it is maintained in that stretched condition for a period of time, will be able to stretch even more. This is the best way to establish or reestablish a range of motion in the soft tissues around a joint, as it does not involve damaging the tissue.

Accordingly, with an orthosis in accordance with the present invention, a patient can apply force to stretch tissue a desired mount by moving the orthosis from a first position to a second position. The patient can then stop applying force to the orthosis. The orthosis remains in the second position. The patient allows the tissue to remain in the stretched condition. The patient can then apply force to stretch tissue a further desired amount by moving the orthosis from the second position to a third position. This repeated stretching and resting of the tissue properly reestablishes a range of motion in the joint.

The orthosis may include means for monitoring, controlling, and/or limiting the amount of force applied by the orthosis, or the range of motion of the orthosis. This can be done in many different ways. A few illustrative methods are shown and described next.

Figure 14:
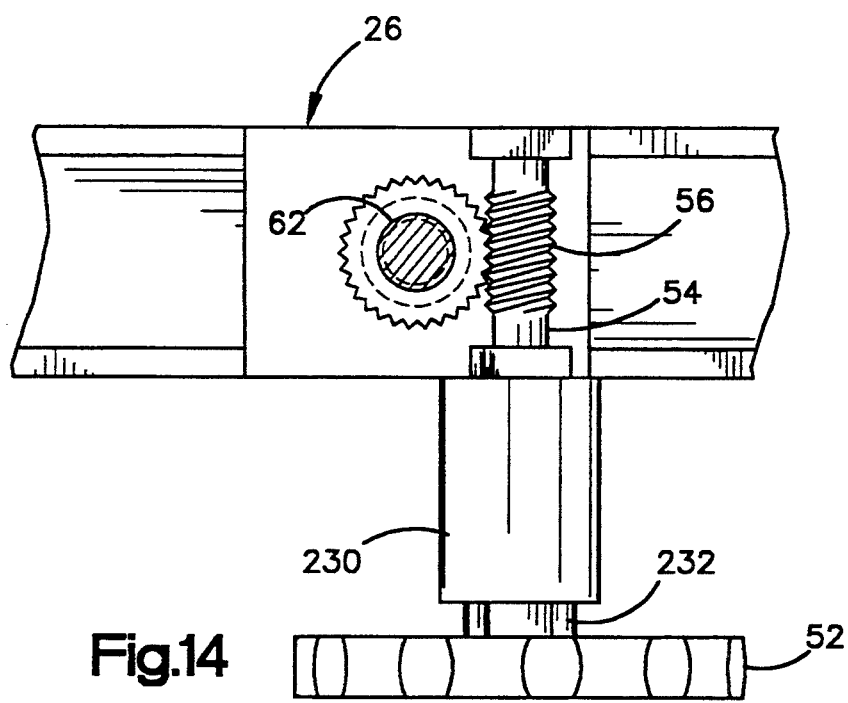
FIG. 14 is a view similar to FIG. 13 illustrating a ratchet drive in the drive mechanism.

One method is by providing wrench flats 232 as shown in FIG. 14 on the shaft 54 connected to the knob 52. A torque wrench can be applied to the wrench flats 232, and the shaft 54 can be turned with the torque wrench. Thus, the patient will know how much torque it takes to turn the shaft at any point during extension or flexion. This can be translated in various ways into an indication of how much force is being applied to the joint.

Another way of monitoring, controlling, and/or limiting the mount of force applied by the orthosis, when the orthosis includes an electric motor drive, involves measuring the work being performed by the electric motor. A torque sensor indicated schematically at 234 (FIG. 6), which may be of a known construction, measures the torque on the lead screw 154 of the drive mechanism. This value is indicative of the work being performed by the motor 150 and of the force applied to the joint. Alternatively, the microprocessor 160 may include circuitry of a known construction for measuring the current drawn by the electric motor 150. Again, this value is indicative of the work being performed by the motor 150 and thus of the force being applied to the joint.

Figure 13:
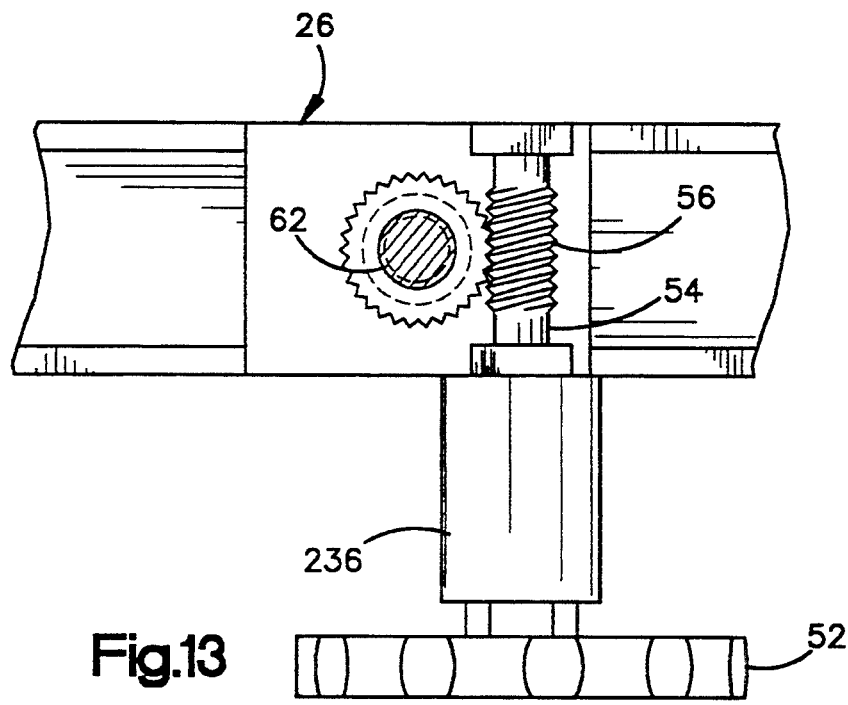
FIG. 13 is a view of a portion of an orthosis including a slip clutch in the drive mechanism.

To provide a positive limiting of the force applied to the joint, a slip clutch can be placed in the drive mechanism. For example, in FIG. 13 there is illustrated a slip clutch 236 of a known construction, in the line of force transmission between the knob 52 and the shaft 54. The slip clutch 236 blocks transmission of force above a certain amount. Thus, no matter how much the patient turns the knob 52, an excessive mount of force is not applied to the joint. The slip clutch 236 can be of the type which is settable to a given force value, and the orthosis may thus be individualized for each patient and/or each therapy session.

Another method of limiting force applied to the joint tissues is to provide phyical "stops" on the orthosis for limiting the range of motion of the orthosis and thus of the joint. There are many readily conceivable ways of doing this, and so they are not described in further detail herein.

In accordance with a further feature of the present invention, the drive mechanism for the cuff arms can be easily and quickly disengaged in case the patient wants to release force on the joint being moved.

Figure 17:
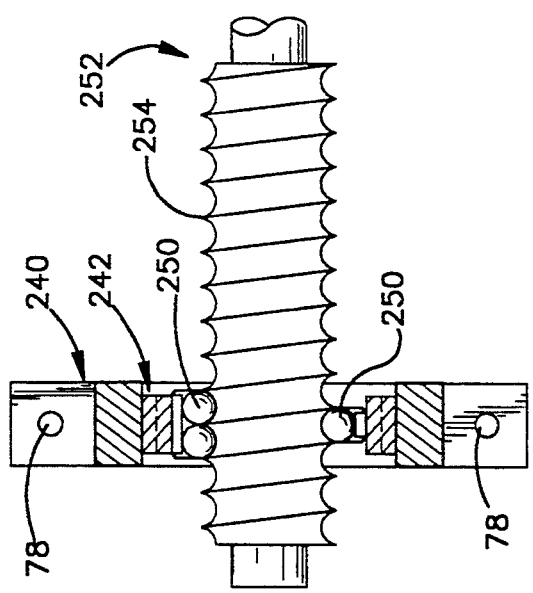
FIG. 17 is a front elevational of the lead screw and arm actuator block of FIG. 15.

An arm actuator block 240 (FIGS. 15-17) includes the openings 78 for the pins 76 which connect the lever arms to the arm actuator block 240. A slider 242 is slidably received in the arm actuator block 240. The slider 242 is fixed for axial movement with the arm actuator block 240. The slider 242 has two leg portions 244. Each leg portion has a cam slot 248. One or more ball members 250 is disposed between each leg portion and a lead screw 252, which preferably has a ball screw thread 254 formed thereon as best seen in FIG. 17. The ball members 250 are fixed for axial movement with the slider 242 and the arm actuator block 240.

A handle 256 including a push button 258 mad a rod member 260 is fixed to and projects outwardly from the slider 242. The rod member 260 extends through a slot in the front plate (not shown) of the tower. The handle 256 is manually operable to move the slider 242 from a first position as shown in FIG. 15 to a second position as shown in FIG. 16.

Figure 15:
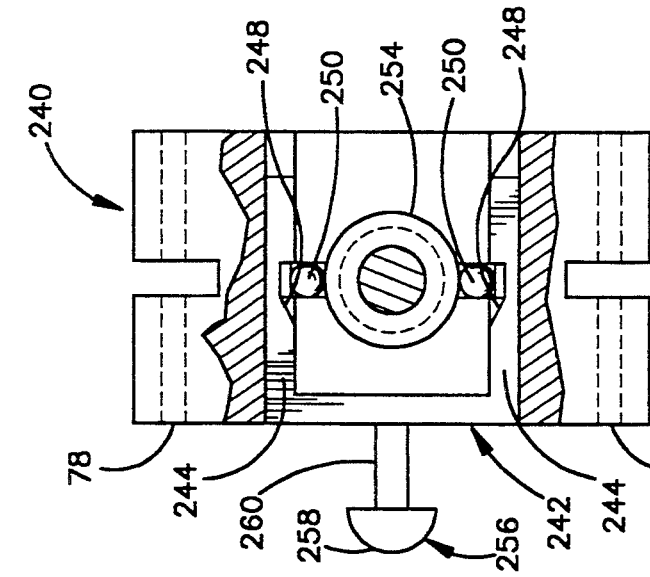
FIG. 15 is a top plan view of an arm actuator block that is disengageable from a ball thread lead screw, in an engaged condition.

When the slider 242 is in the first position as illustrated in FIG. 15, the ball members 250 are cammed radially inwardly into engagement with the ball screw thread 254 on the lead screw 252. Rotation of the lead screw 252 causes axial movement of the ball members 250, and thus results in axial movement of the slider 242 and of the arm actuator block 240. Axial movement of the arm actuator block 240, as described above, causes relative movement of the orthosis arms.

Figure 16:
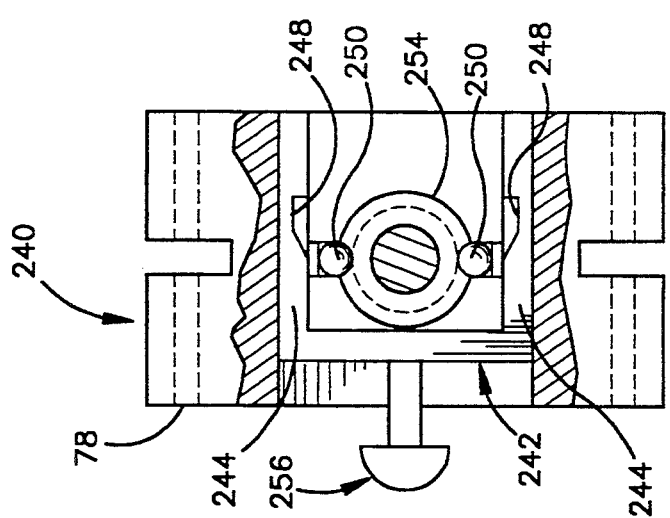
FIG. 16 is a view similar to FIG. 16, with the arm actuator block in a disengaged condition.

When the slider 242 is in the second position as shown in FIG. 16, the ball members 250 are cammed radially outwardly, by the ball screw thread 254, into the cam slots 248 in the slider leg portions 244. In this position, the ball members 250 are disengaged from the ball screw thread 254 of the lead screw 252. Rotation of the lead screw 252 does not result in axial movement of the ball members 250, the slider 242, or the arm actuator block 240.

Thus, there is provided an effective apparatus for disengaging the drive mechanism of an orthosis in accordance with the present invention. It is to be understood that other suitable mechanisms can be provided and are within the scope of the invention.

Figure 18:
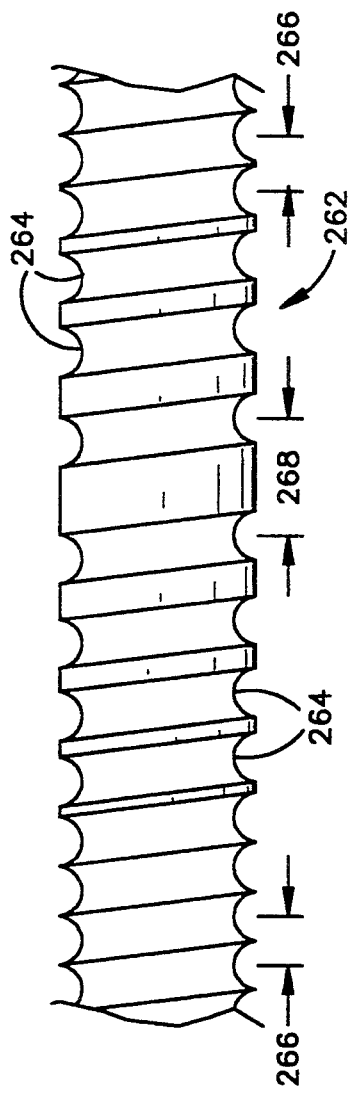
FIG. 18 is a schematic front elevational of a variable pitch lead screw.

A gear drive mechanism for an orthosis of the present invention may include variable ratio gearing. For example, the lead screw 252 illustrated in FIG. 17 may be replaced with a lead screw 262 as illustrated in FIG. 18 which has a variable pitch. The gear teeth represented at 264 are closer together at the axial ends of the lead screw 262 than in the middle. The pitch 266 between adjacent teeth at the ends of the lead screw 262 is less than the pitch 268 between adjacent teeth at the center of the lead screw 262. Thus, an arm actuator block engaging the lead screw 262 will gain less axial motion at the extremes of motion, per revolution of the lead screw, than in the middle of the range of motion.

As noted above, because of the mechanical advantage provided by the drive mechanism and by the tower, an orthosis constructed in accordance with the present invention is lightweight and easily usable by the patient alone. If the orthosis is used on an elbow joint, the patient can use the orthosis while seated upright, with his arm on a suitable rest such as on a table, for example. If the orthosis is used for CPM on a knee joint, that is, cycling between flexion and extension, the patient can use it while seated in a chair. Such use of the orthosis of the present invention is highly preferable to the typical knee therapy which requires that the patient be lying in bed.

Figure 19:
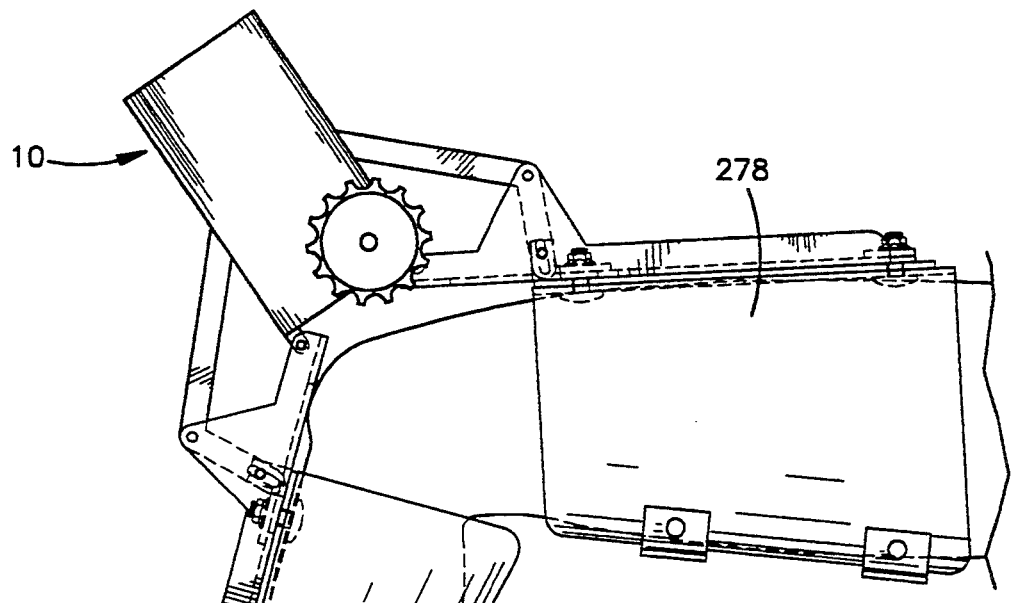
FIG. 19 is a view of an orthosis being used in combination with a rollable foot rest for knee therapy.
Figure 20:
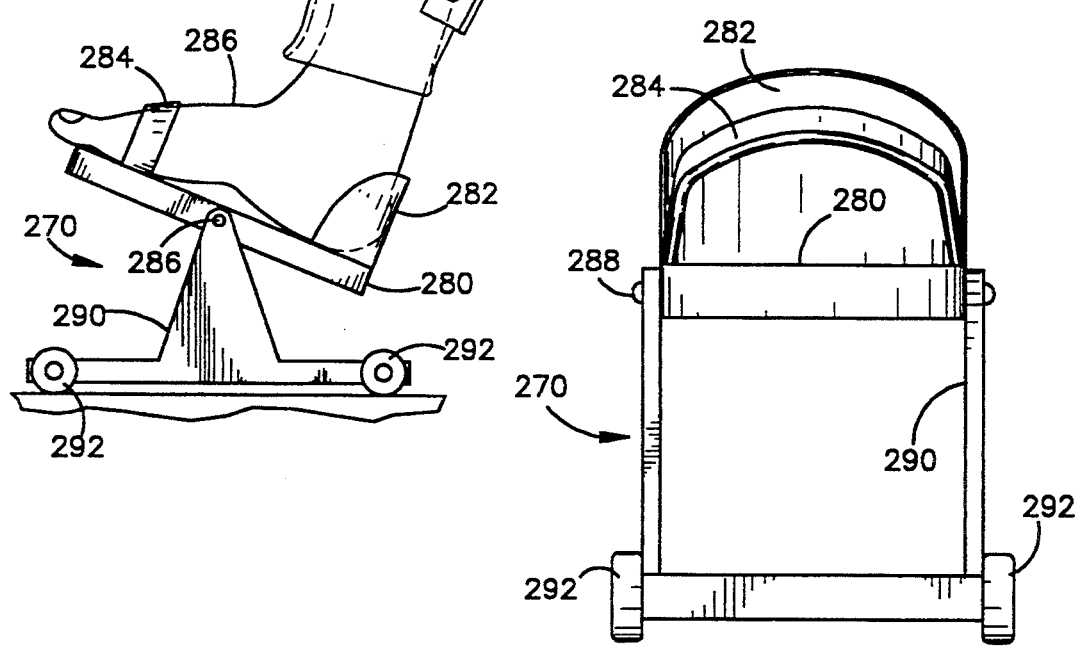
FIG. 20 is an end view of the foot rest of FIG. 19.

When the orthosis is used on a knee with a seated patient, it is desirable to provide, under the patient's foot, a device such as the foot support 270 illustrated in FIGS. 19-20. FIG. 19 illustrates an orthosis 10 as illustrated in FIGS. 1-5. The orthosis 10 is in position to flex and extend a knee joint 272. The knee joint is located between an upper leg 274 and a lower leg 276. A cuff 278 is attached to the upper leg 274. A cuff 279 is attached to the lower leg 276.

The foot support 270 includes a footrest 280. A heel cup 282 is fixed on the foot rest 280. An adjustable strap 284 secures the patient's foot 286 on the foot rest 280. The foot rest 280 is pivotally mounted at 268 to a frame 290. A plurality of rollers 292 are attached to the frame 290. The rollers 292 are rollable on the floor (not shown) underneath the patient. The foot support 270 allows the patient's foot 286 to move back and forth along the floor with minimal resistance. This permits the orthosis 10 to flex and extend the knee joint 272 easily. Thus, the patient can conveniently use the orthosis 10 on his knee joint while in any position such as a comfortable seated position, as compared to the difficulty and inconvenience of therapy while lying in a bed. Of course, the present orthosis can also be used while the patient is lying in bed.

It should also be noted that the orthoses of the present invention are suitable to hyperextend a joint, so that a slight overcorrection may be obtained if needed. Preferably, the orthosis is constructed so that the joint may be hyperextended by 5° to 7°. This provides the fullest range of motion desired. This can be accomplished by construction of the pivotal connection between the tower and the cuff arms to allow for such hyperextension.

The lever arms of the various orthoses illustrated are rigid members made of, for example, a metal such as aluminum or stainless steel so as to be able to transmit the necessary forces. It should be understood that any material of sufficient rigidity can be used, including a polymeric or composite material.

It is apparent that the orthosis of the present invention can apply much greater forces, safely through any range of motion, as compared to a spring-driven orthosis such as in the prior art. It is further apparent that the orthosis of the present invention attempts to limit compression of a joint through the joint's entire range of motion.

Further, it can be seen that the orthosis of the present invention is usable with the patient seated or in a lying position as opposed to a prior art device which can be used solely while lying in bed, and is thus more comfortable. The orthosis is light weight and portable, because of the mechanical advantage of the drive mechanism and the small power source needed. The orthosis provides both a manual stretching device and an electric CPM device with a manual override. The orthosis can be used to stretch tissue to increase range of motion, or to cycle through the range of motion to maintain it, or both. The orthosis can, when properly dimensioned, be used on any joint. It can also be used for motion other than flexion and extension, such as rotation, pronation, supination, etc., when suitably modified while incorporating the same operating principles.

From the above description of the invention, those skilled in the art will perceive improvements, changes and modifications in the invention. Such improvements, changes and modifications within the skill of the art are intended to be covered by the appended claims.

We claim:

1. An orthosis movable between first and second conditions for moving a joint which is located between first and second relatively movable body portions, comprising:
   a first cuff arm;
   a second cuff arm movably connected to said first cuff arm;
   a first cuff on said first cuff arm for connecting said first cuff arm to the first body portion;
   a second cuff on said second cuff arm for connecting said second cuff arm to the second body portion;
   means for moving said first cuff arm relative to said second cuff arm about an axis intermediate said first and second cuffs; and
   means for moving said first cuff along said first cuff arm upon relative movement between said first and second cuff arms, said means for moving said first cuff along said first cuff arm includes a motor and linkage means for transmitting force from said motor to said first cuff to move said first cuff along said first cuff arm through a distance which is a function of the extent of movement of said first cuff arm relative to said second cuff arm.

2. An orthosis as defined in claim 1 wherein said first cuff is slidably mounted on said first cuff arm.

3. An orthosis as defined in claim 2 wherein said first cuff arm comprises a track having at least one slot extending longitudinally along said track, said first cuff including means for extending through said slot and for guiding the sliding movement of said first cuff on said first cuff arm.

4. An orthosis as defined in claim 3 wherein said means for moving said first cuff upon relative movement between said first and second cuff arms comprises a cuff actuator block fixed to said first cuff and slidably mounted on said first cuff arm, said cuff actuator block being slidably driven by said means for moving said first cuff arm relative to said second cuff arm.

5. An orthosis for stretching tissue around a joint between first and second relatively pivotable body portions, comprising:
   a first cuff arm, and a first cuff on said first cuff arm for connecting said first cuff arm to the first body portion;
   a second cuff arm movably connected to said first cuff arm, and a second cuff on said second cuff arm for connecting said second cuff arm to the second body portion;
   means for moving said first cuff arm relative to said second cuff arm;
   means for moving said first cuff on said first cuff arm and for moving said second cuff on said second cuff arm upon relative movement between said first and second cuff arms; and
   said means for moving said first cuff arm relative to said second cuff arm being selectively operable to provide incremental movement of said first cuff arm relative to said second cuff arm between a plurality of positions and to lock said arms at said positions.

6. An orthosis as defined in claim 5 wherein said means for moving said first cuff arm relative to said second cuff arm comprises ratchet drive means.

7. An orthosis as defined in claim 5 wherein said means for moving said first cuff arm relative to said second cuff arm comprises gear drive means.

8. An apparatus effecting relative movement between first and second body portions interconnected by a joint, said apparatus comprising a first cuff arm, first cuff means for connecting said first cuff arm with the first body portion, said first cuff means being movable along said first cuff arm, a second cuff arm, second cuff means for connecting said second cuff arm with the second body portion, means for interconnecting said first and second cuff arms and for enabling said first cuff arm to move relative to said second cuff arm, and fluid motor means operable under the influence of fluid pressure and connected with at least said first cuff arm for moving said first cuff arm relative to said second cuff arm and to simultaneously therewith move said first cuff means along said first cuff arm.

9. An apparatus as set forth in claim 8 wherein said second cuff means is movable along said second cuff arm, said fluid motor means being operable to move said second cuff arm and to simultaneously therewith move said second cuff means along said second cuff arm.

10. An apparatus as set forth in claim 9 further including a first lever having a first end portion connected with said fluid motor means and a second end portion connected with said first cuff means, said first lever being connected with said first cuff arm at a location between said first and second end portions of said first lever, said fluid motor means being operable to move said first end portion of said first lever to move said second end portion of said first lever and said first cuff means relative to said first cuff arm.

11. An apparatus as set forth in claim 10 further including a second lever having a first end portion connected with said fluid motor means and a second end portion connected with said second cuff means, said second lever being connected with said second cuff arm at a location between said first and second end portions of said second lever, said fluid motor means being operable to move said first end portion of said second lever to move said second end portion of said second lever and said second cuff means relative to said second cuff arm.

12. An apparatus for effecting relative movement between first and second body portions interconnected by a joint, the joint and first and second body portions defining on one side of the joint an inner sector which decreases in angle as the joint is flexed and define on the opposite side of the joint an outer sector which decreases in angle as the joint is extended, said apparatus comprising a first cuff arm disposed in the outer sector and having a first end portion adjacent to the joint, first cuff means for connecting said first cuff arm with the first body portion, said first cuff means being movable along said first cuff arm, a second cuff arm disposed in the outer sector and having a first end portion adjacent to the joint, said first end portion of said second cuff arm being spaced from said first end portion of said first cuff arm, second cuff means for connecting said second cuff arm with the second body portion, said second cuff means being movable along said second cuff arm, a connector member disposed in the outer sector and having a first end portion connected to the first end portion of said first cuff arm at a first pivot connection disposed in the outer sector, said connector member having a second end portion connected to the first end portion of said second cuff arm at a second pivot connection disposed in the outer sector, and drive means connected with said first and second cuff arms for effecting pivotal movement between said first and second cuff arms relative to said connector member at said first and second pivot connections and simultaneously therewith effecting movement of said first and second cuff means along said first and second cuff arms to effect relative movement between the first and second body portions.

13. An apparatus as set forth in claim 12 further including means for applying force to said first and second cuff means to distract the joint simultaneously with pivotal movement of said first and second cuff arms relative to said connector member at said first and second pivot connections.

14. An apparatus as set forth in claim 12 wherein said drive means includes a fluid motor which is connected with said first and second cuff arms and is operable under the influence of fluid pressure to pivot said first and second cuff arms relative to said connector member.

15. An apparatus as set forth in claim 14 wherein said fluid motor is disposed in the outer sector and is connected with said connector member.

16. An apparatus as set forth in claim 12 wherein said first and second cuff means are movable away from said first and second pivot connections during operation of said drive means in one direction, said first and second cuff means being movable toward said first and second pivot connections during operation of said drive means in a direction opposite to the one direction.

17. An apparatus as set forth in claim 12 wherein said first cuff means is movable along said first cuff arm in a direction away from said first pivot connection and in a direction toward said first pivot connection, said apparatus further including force transmitting means for transmitting force from said drive means to move said first cuff means along said first cuff arm in the direction away from said first pivot connection upon operation of said drive means in one direction and for transmitting force from said drive means to move said first cuff means in the direction toward said first pivot connection during operation of said drive means in a direction opposite to the one direction.

18. An apparatus as set forth in claim 17 wherein said drive means includes a fluid motor and means for connecting said fluid motor with said first cuff arm and said force transmitting means.

19. An apparatus as set forth in claim 12 wherein said drive means is mounted on said connector member and is at least partially located in the outer sector.

20. An apparatus as set forth in claim 12 wherein said drive means includes an externally threaded member and an internally threaded member which is disposed in engagement with said externally threaded member, said internally and externally threaded members being relatively movable to effect pivotal movement of at least one of said first and second cuff arms relative to said connector member.

21. An apparatus for effecting relative movement between first and second body portions interconnected by a joint, the joint and first and second body portions defining on one side of the joint an inner sector which decreases in angle as the joint is flexed and define on the opposite side of the joint an outer sector which decreases in angle as the joint is extended, said apparatus comprising a first cuff arm disposed in the outer sector and having a first end portion adjacent to the joint, first cuff means for connecting said first cuff arm with the first body portion, a second cuff arm disposed in the outer sector and having a first end portion adjacent to the joint, said first end portion of said second cuff arm being spaced from said first end portion of said first cuff arm, second cuff means for connecting said second cuff arm with the second body portion, a connector member disposed in the outer sector and having a first end portion connected to the first end portion of said first cuff arm at a first pivot connection disposed in the outer sector, said connector member having a second end portion connected to the first end portion of said second cuff arm at a second pivot connection disposed in the outer sector, and force transmitting means for moving said first cuff means away from said first pivot connection as the joint is flexed and for moving said first cuff means toward said first pivot connection as the joint is extended.

22. An apparatus as set forth in claim 21 wherein said force transmitting means includes means for moving said second cuff means away from said second pivot connection as the joint is flexed and for moving said second cuff means toward said second pivot connection as the joint is extended.

23. An apparatus as set forth in claim 21 wherein said force transmitting means includes an externally threaded member and an internally threaded member which is disposed in engagement with said externally threaded member, said internally and externally threaded members being relatively movable in a first direction to effect movement of said first cuff means away from said first pivot connection and being relatively movable in a second direction to effect movement of said first cuff means toward said first pivot connection.

24. An apparatus as set forth in claim 23 wherein said internally and externally threaded members are disposed in the outer sector.

25. An apparatus as set forth in claim 21 further including a fluid motor which is operable under the influence of fluid pressure to effect operation of said force transmitting means and movement of said first cuff means relative to said first pivot connection.

26. An apparatus as set forth in claim 21 wherein said force transmitting means is operable to effect pivotal movement between said first and second cuff arms relative to said connector member at said first and second pivot connections during movement of said first cuff means away from said first pivot connection and during movement of said first cuff means toward said first pivot connection.

27. An apparatus as set forth in claim 26 further including drive means connected with said force transmitting means for effecting operation of said force transmitting means.

28. An apparatus for effecting relative movement between first and second body portions interconnected by a joint, the joint and first and second body portions defining on one side of the joint an inner sector which decreases in angle as the joint is flexed and define on the opposite side of the joint an outer sector which decreases in angle as the joint is extended, said apparatus comprising a first cuff arm disposed in the outer sector and having a first end portion adjacent to the joint, first cuff means for connecting said first cuff arm with the first body portion, a second cuff arm disposed in the outer sector and having a first end portion adjacent to the joint, said first end portion of said second cuff arm being spaced from said first end portion of said first cuff arm, second cuff means for connecting said second cuff arm with the second body portion, connector means disposed in the outer sector for pivotally interconnecting said first and second cuff arms, force transmitting means for effecting pivotal movement between said first and second cuff arms in a first direction to flex the joint and for effecting pivotal movement between said first and second cuff arms in a second direction to extend the joint, said force transmitting means including means for moving said first cuff means away from said connector means during pivotal movement between said first and second cuff arms in the first direction and for moving said first cuff means toward said connector means during pivotal movement between said first and second cuff arms in the second direction.

29. An apparatus as set forth in claim 28 further including fluid motor means connected with said force transmitting means and operable under the influence of fluid pressure to effect operation of said force transmitting means.

30. An apparatus as set forth in claim 28 wherein said force transmitting means includes an externally threaded member and an internally threaded member which is disposed in engagement with said externally threaded member, said internally and externally threaded members being relatively movable in a one direction to effect movement of said first cuff means away from said connector means and being relatively movable in a direction opposite to effect movement of said first cuff means toward said connector means.

31. An apparatus as set forth in claim 30 wherein said internally and externally threaded members are disposed in the outer sector.

32. An apparatus as set forth in claim 28 wherein said force transmitting means includes an externally threaded member and an internally threaded member which is disposed in engagement with said externally threaded member, said internally and externally threaded members being relatively movable in one direction to effect pivotal movement between said first and second cuff arms in the first direction and to effect movement of said first cuff means away from said connector means, said internally and externally threaded members being relatively movable in a direction opposite to the one direction to effect pivotal movement between said first and second cuff arms in the second direction and to effect movement of said first cuff means toward said connector means.

33. An apparatus as set forth in claim 32 further including motor means for effecting relative movement between said internally and externally threaded members, said motor means and said internally and externally threaded members being disposed in the outer sector.

34. An apparatus effecting relative movement between first and second body portions interconnected by a joint, said apparatus comprising a first cuff arm, first cuff means for connecting said first cuff arm with the first body portion, said first cuff means being movable along said first cuff arm, a second cuff arm, second cuff means for connecting said second cuff arm with the second body portion, said second cuff means being movable along said second cuff arm, a connector interconnecting said first and second cuff arms to enable said first cuff arm to move relative to said second cuff arm, and a motor connected with at least said first cuff arm and operable to move said first cuff arm relative to said second cuff arm, said motor being connected with said first cuff means and being operable to move said first cuff means along said first cuff arm, said motor being connected with said second cuff means and being operable to move said second cuff means along said second cuff arm.

35. An apparatus as set forth in claim 34 wherein said motor includes a fluid motor which is operable under the influence of fluid pressure.

36. An apparatus as set forth in claim 34 further including linkage means for transmitting force from said motor to said first cuff arm and to said first cuff means to effect movement of said first cuff arm relative to said second cuff arm and to simultaneously therewith effect movement of said first cuff means relative to said first cuff arm and for transmitting force from said motor to said second cuff means to effect movement of said second cuff means relative to said second cuff arm simultaneously with movement of said first cuff means relative to said first cuff arm.

37. An apparatus as set forth in claim 36 wherein said motor includes a fluid motor which is operable under the influence of fluid pressure.

38. An apparatus effecting relative movement between first and second body portions interconnected by a joint, said apparatus comprising a first cuff arm, first cuff means for connecting said first cuff arm with the first body portion, said first cuff means being movable along said first cuff arm, a second cuff arm connected with said first cuff arm, second cuff means for connecting said second cuff arm with the second body portion, a motor, and a linkage connecting said motor with at least one of said first and second cuff arms and with said first cuff means, said motor being operable to actuate said linkage to move said first cuff means along said first cuff arm under the influence of force transmitted from said motor to said first cuff means by said linkage and to effect movement between said first and second cuff arms under the influence of force transmitted from said motor to said first cuff arm by said linkage.

39. An apparatus as set forth in claim 38 wherein said second cuff means is movable along said second cuff arm, said linkage connecting said motor with said second cuff arm and said second cuff means, said motor being operable to actuate said linkage to move said second cuff means along said second cuff arm under the influence of force transmitted from said motor to said second cuff means simultaneously with movement of said first cuff means along said first cuff arm.

40. An apparatus as set forth in claim 39 wherein said motor is a fluid motor which is operable under the influence of fluid pressure.

41. An apparatus as set forth in claim 39 wherein said motor is an electric motor, said electric motor being connected with said linkage by a screw member which is rotatable by said electric motor.

42. An apparatus as set forth in claim 38 further including a connector which extends between end portions of said first and second cuff arms, a first connection pivotably connecting said connector with said end portion of said first cuff arm, and a second connection pivotally connecting said connector with said end portion of said second cuff arm, said motor being mounted on said connector.

43. An apparatus as set forth in claim 42 wherein said motor is operable in one direction to move a portion of said linkage toward said connector to actuate said linkage to move said first cuff means along said first cuff arm in a first direction, said motor being operable in another direction which is opposite to the one direction to move a portion of said linkage away from said connector to actuate said linkage to move said first cuff means along said first cuff arm in a second direction which is opposite to the first direction.

44. An apparatus as set forth in claim 43 wherein said motor is a fluid motor which is operable under the influence of fluid pressure.

45. An apparatus as set forth in claim 43 wherein said motor is an electric motor.

46. An apparatus as set forth in claim 38 wherein said linkage includes a link having a first end portion connected with said motor, said link having a second end portion connected with said first cuff means, said link having a third portion which is pivotally connected with said first cuff arm, said motor being operable to move said first end portion of said link to move said first cuff arm relative to said second cuff arm under the influence of force transmitted from said motor through the first end portion of said link to the third portion of said link and to move said first cuff means along said first cuff arm under the influence of force transmitted from said motor through the first end portion of said link to the second end portion of said link.

47. An apparatus as set forth in claim 46 wherein said motor is an electric motor, said electric motor being connected with said first end portion of said link through a screw member which is rotatable by said electric motor to move said first end portion of said link.

48. An apparatus as set forth in claim 46 wherein said motor is a fluid motor which is operable under the influence of fluid pressure, said fluid motor being connected with said first end portion of said link and being operable under the influence of fluid pressure to move said first end portion of said link.

49. An apparatus as set forth in claim 46 wherein said second end portion of said link is connected with said first cuff means by a pin-and-slot connection which enables a location where force is transmitted between said second end portion of said link and said first cuff means to be varied relative to a pivot connection between said third portion of said link and said cuff arm during movement of said link by said motor.

50. An apparatus as set forth in claim 49 wherein said motor is reversible to enable said motor to be operated in one direction to actuate said linkage and move said first cuff means along said first cuff arm in a first direction and to enable said motor to be operated in another direction opposite to said one direction to actuate said linkage and move said first cuff means along said first cuff arm in a second direction opposite to said first direction.

51. An apparatus as set forth in claim 50 wherein said motor is an electric motor.

52. An apparatus as set forth in claim 50 wherein said motor is a fluid motor which is operated under the influence of fluid pressure.

53. An apparatus for effecting relative movement between first and second body portions interconnected by a joint, said apparatus comprising a first cuff arm having a first end portion adjacent to the joint, first cuff means for connecting said first cuff arm with the first body portion, said first cuff means being movable along said first cuff arm, a second cuff arm having a first end portion adjacent to the joint, said first end portion of said second cuff arm being spaced from said first end portion of said first cuff arm, second cuff means for connecting said second cuff arm with the second body portion, a connector member having a first end portion connected to the first end portion of said first cuff arm at a first pivot connection, said connector member having a second end portion connected to the first end portion of said second cuff arm at a second pivot connection, and drive means connected with said first and second cuff arms for effecting pivotal movement between said first and second cuff arms and for simultaneously therewith effecting movement of said first cuff means along said first cuff arm, said drive means including a motor mounted on said connector member and a linkage connecting said motor with said first and second cuff arms and with said first cuff means.

54. An apparatus as set forth in claim 53 wherein said motor is a fluid motor which is operable under the influence of fluid pressure to actuate said linkage.

55. An apparatus as set forth in claim 53 wherein said motor is an electric motor, said drive means further including a threaded member which is rotatable by said electric motor.

56. An apparatus as set forth in claim 53 wherein said motor is operable in one direction to actuate said linkage to move said first cuff means along said first cuff arm in a first direction, said motor being operable in another direction opposite to said one direction to actuate said linkage to move said first cuff means along said first cuff arm in a second direction opposite to said first direction.

57. An apparatus as set forth in claim 53 wherein said drive means includes a rotatable screw member connected with said motor and said linkage, said motor being operable to rotate said screw member to actuate said linkage to effect pivotal movement between said first and second cuff arms and to effect movement of said first cuff means along said first cuff arm under the influence of force transmitted from said motor through said screw member to said linkage.

58. An apparatus as set forth in claim 53 wherein said drive means includes a manually actuatable input member connected with said linkage and movable under the influence of manually applied force to actuate said linkage to effect pivotal movement between said first and second cuff arms and to simultaneously therewith effect movement of said first cuff means along said first cuff arm with said motor in an inactive condition in which said motor is ineffective to provide force to actuate said linkage.

59. An apparatus as set forth in claim 53 further including a disconnect mechanism connected with said motor and said linkage, said disconnect mechanism being operable between an engaged condition in which force can be transmitted between said motor and said linkage and a disengaged condition preventing the transmission of force between said motor and said linkage and enabling said linkage to be moved relative to said motor.

60. An apparatus as set forth in claim 53 wherein said drive means includes an internally threaded member and an externally threaded member which are disposed in threaded engagement and are connected with said motor and said linkage, one of said threaded members being rotatable by said motor to move the other one of said threaded members to actuate said linkage.

61. An apparatus as set forth in claim 53 wherein said linkage includes a rigid link having a first portion connected with said motor, a second portion connected with said first cuff means, and third portion pivotally connected with said first cuff arm, said motor being operable in one direction to pivot said link relative to said first cuff arm and move said first cuff means in a first direction along said first cuff arm, said motor being operable in another direction opposite to the one direction to pivot said link relative said first cuff arm and move said first cuff means along said first cuff arm in a second direction which is opposite to the first direction.

62. An apparatus for effecting relative movement between first and second body portions interconnected by a joint which is capable of being flexed and extended, said apparatus comprising a first cuff arm having a first end portion adjacent to the joint and a second end portion spaced further from the joint than said first end portion of said first cuff arm, first cuff means for connecting said first cuff arm with the first body portion, said first cuff means being movable relative to said first cuff arm, a second cuff arm having a first end portion adjacent to the joint and a second end portion spaced further from the joint than said first end portion of said second cuff arm, said first end portion of said second cuff arm being spaced from said first end portion of said first cuff arm, second cuff means for connecting said second cuff arm with the second body portion, a connector member having a first portion connected to the first end portion of said first cuff arm at a first pivot connection, said connector member having a second portion connected to the first end portion of said second cuff arm at a second pivot connection, and drive means connected with said first and second cuff arms and said first cuff means for pivoting said first and second cuff arms relative to said connector member at said first and second pivot connections to move said second end portions of said first and second cuff arms toward each other to flex the joint and for moving said first cuff means relative to said first cuff arm in a direction away from said first pivot connection during flexion of the joint, said drive means being operable to pivot said first and second cuff arms relative to said connector member at said first and second pivot connections to move said second end portions of said first and second cuff arms away from each other and to move said first cuff means relative to said first cuff arm in a direction toward said first pivot connection during extension of the joint.

63. An apparatus as set forth in claim 62 wherein said drive means includes a fluid motor operable under the influence of fluid pressure to provide force to move said first and second cuff arms relative to each other and to move said first cuff means relative to said first cuff arm.

64. An apparatus as set forth in claim 62 wherein said drive means includes an electric motor which is operable to provide force to move said first and second cuff arms relative to each other and to move said first cuff means relative to said first cuff arm.

65. An apparatus as set forth in claim 62 wherein said drive means includes a motor and a linkage connecting said motor with said first cuff arm and said first cuff means, said linkage being operable to transmit force from said motor to said first cuff arm to pivot said first cuff arm about said first pivot connection and to transmit force from said motor to said first cuff means to move said first cuff means relative to said first cuff arm.

66. An apparatus as set forth in claim 62 wherein said drive means includes a linkage which is connected with said first and second cuff arms and with said first cuff means, said linkage including a base link which is movable toward and away from said connector member along a linear path having a longitudinal axis which extends through said connector member and a plurality of connector links which are pivotally connected with said base link and with said first and second cuff arms and with said first cuff means to transmit force from said base link to said first and second cuff arms and to said first cuff means.

67. An apparatus as set forth in claim 66 wherein said drive means includes a motor connected with said connector member and said base link, said motor being operable in a first direction to move said base link toward said connector member and being operable in a second direction to move said base link away from said connector member.

68. An apparatus as set forth in claim 67 wherein said motor is a fluid motor which is operable under the influence of fluid pressure.

69. An apparatus as set forth in claim 67 wherein said motor is an electric motor.

70. An apparatus as set forth in claim 67 wherein said drive means includes an internally threaded member and an externally threaded member disposed in threaded engagement with said internally threaded member, a first one of said threaded members being connected with said base link and being movable with said base link relative to said connector member, a second one of said threaded members being connected with said motor and being rotatable by said motor to effect movement of said base link relative to said connector member.

71. An apparatus as set forth in claim 67 wherein said drive means includes a connector link having a first end portion which is pivotally connected with said base link, a second end portion which is pivotally connected with said first cuff means, and an intermediate portion which is pivotally connected with said first cuff arm.

72. An apparatus as set forth in claim 62 wherein said second cuff means is movable relative to said second cuff arm, said drive means being connected with said second cuff means and being operable to move said second cuff means relative to said second cuff arm in a direction away from said second pivot connection during flexion of the joint, said drive means being operable to move said second cuff means relative to said second cuff arm in a direction toward said second pivot connection during extension of the joint.

73. An apparatus as set forth in claim 72 wherein said drive means includes a motor and a linkage connecting said motor with said first and second cuff arms and with said first and second cuff means, said linkage being operable to transmit force from said motor to said first and second cuff arms to pivot said first cuff arm about said first pivot connection and to pivot said second cuff arm about said second pivot connection, said linkage being operable to transmit force from said motor to said first cuff means to move said first cuff means relative to said first cuff arm and to transmit force from said motor to said second cuff means to move said second cuff means relative to said second cuff arm.

74. An apparatus as set forth in claim 72 wherein said drive means includes a linkage which is connected with said first and second cuff arms and with said first and second cuff means, said linkage including a base link which is movable toward and away from said connector member and a plurality of connector links which are pivotally connected with said base link and with said first and second cuff arms and with said first and second cuff means to transmit force from said base link to said first and second cuff arms and to said first and second cuff means.

75. An apparatus as set forth in claim 74 wherein said drive means include a motor connected with said connector member and said base link, said motor being operable in a first direction to move said base link toward said connector member and being operable in a second direction to move said base link away from said connector member.

76. An apparatus as set forth in claim 75 wherein said drive means includes an internally threaded member and an externally threaded member disposed in threaded engagement with said internally threaded member, a first one of said threaded members being connected with said base link and being movable with said base link relative to said connector member, a second one of said threaded members being connected with said motor and being rotatable by said motor to effect movement of said base link relative to said connector member.

77. An apparatus as set forth in claim 75 wherein a first one of said connector links of said plurality of connector links has a first portion which is pivotally connected with said base link, a second portion which is pivotally connected with said first cuff means, and a third portion which is pivotally connected with said first cuff arm, a second one of said connector links of said plurality of connector links having a first portion which is pivotally connected with said base link, a second portion which is pivotally connected with said second cuff means, and a third portion which is pivotally connected with said second cuff arm.

78. An apparatus as set forth in claim 77 wherein said motor is a fluid motor which is operable under the influence of fluid pressure.

79. An apparatus as set forth in claim 77 wherein said motor is an electric motor.

80. An apparatus for effecting relative movement between first and second body portions interconnected by a joint, said apparatus comprising a first cuff arm having a first end portion adjacent to the joint, first cuff means for connecting said first cuff arm with the first body portion, said first cuff means being movable along said first cuff arm, a second cuff arm having a first end portion adjacent to the joint, said first end portion of said second cuff arm being spaced from said first end portion of said first cuff arm, second cuff means for connecting said second cuff arm with the second body portion, said second cuff means being movable along said second cuff arm, a connector member having a first portion connected to the first end portion of said first cuff arm at a first pivot connection, said connector member having a second portion connected to the first end portion of said second cuff arm at a second pivot connection, and a drive assembly connected with said connector member, said first and second cuff arms and said first and second cuff means, said drive assembly being operable to effect pivotal movement of said first and second cuff arms relative to said connector member at said first and second pivot connections and to simultaneously therewith effect movement of said first cuff means along said first cuff arm and movement of said second cuff means along said second cuff arm, said drive assembly includes a linkage which is connected with said first and second cuff arms and with said first and second cuff means, said linkage including a base link which is movable toward and away from said connector member, a first connector link having a first portion pivotally connected with said base link, a second portion connected with said first cuff means and a third portion pivotally connected with said first cuff arm, and a second connector link having a first portion pivotally connected with said base link, a second portion connected with said second cuff means and a third portion pivotally connected with said second cuff arm, said base link being movable in one direction relative to said connector member to transmit force through said first connector link to pivot said first cuff arm in a first direction relative to said connector member and to simultaneously therewith move said first cuff means along said first cuff arm in a direction toward said connector member and to transmit force through said second connector link to pivot said second cuff arm relative to said connector member in a second direction which is opposite to the first direction and to simultaneously therewith move said second cuff means along said second cuff arm in a direction toward said connector member, said base link being movable in a direction opposite to the one direction relative to said connector member to transmit force through said first connector link to pivot said first cuff arm in the second direction relative to said connector member and to simultaneously therewith move said first cuff means along said first cuff arm in a direction away from said connector member and to transmit force through said second connector link to pivot said second cuff arm relative to said connector member in the first direction and to simultaneously therewith move said second cuff means along said second cuff arm in a direction away from said connector member, said drive means further including an input apparatus connected with and at least partially disposed between said connector member and said base link to move said base link relative to said connector member.

81. An apparatus as set forth in claim 80 wherein said input apparatus includes a fluid motor which is operable in one direction under the influence of fluid pressure to effect movement of said base link toward said connector member and being operable in a direction opposite to the one direction of operation of said fluid motor to effect movement of said base link away from said connector member.

82. An apparatus as set forth in claim 80 wherein said input apparatus includes a motor which is operable in one direction to effect movement of said base link toward said connector member and is operable in a direction opposite to the one direction of operation of said motor to effect movement of said base link away from said connector member.

83. An apparatus as set forth in claim 80 wherein said input apparatus includes an internally threaded member and an externally threaded member which is disposed in engagement with said internally threaded member, a first one of said threaded members being connected with said base link and a second one of said threaded members being connected with said connector member, one of said threaded members being rotatable in one direction to move said base link toward said connector member and being rotatable in a direction opposite to the one direction of rotation of said one threaded member to move said base link away from said connector member.

84. An apparatus as set forth in claim 83 wherein said input apparatus further includes a manually actuatable input member connected with said one of said threaded members which is rotatable, said manually actuatable input member being movable under the influence of manually applied force to rotate said one of said threaded members which is rotatable.

85. An apparatus as set forth in claim 83 wherein said input apparatus includes a motor connected with said one of said threaded members which is rotatable, said motor being operable in a first direction to rotate said one of said threaded members in one direction and being operable in a second direction to rotate said one of said threaded members in a direction which is opposite to the one direction of rotation.

86. An apparatus as set forth in claim 80 wherein said input apparatus includes a motor which is mounted on said connector member and is connected with said base link, said motor being operable in one direction to move said base link toward said connector member and being operable in a direction opposite to the one of operation of said motor direction to move said base link away from said connector member.

87. An apparatus as set forth in claim 80 wherein said motor is a fluid motor which is at least partially disposed between said connector member and said base link.

* * * * *

UNITED STATES PATENT AND TRADEMARK OFFICE
CERTIFICATE OF CORRECTION

PATENT NO. : 5,395,303
DATED : March 7, 1995
INVENTOR(S) : Peter M. Bonutti and Gary E. Zitzmann It is certified that error appears in the above-indentified patent and that said Letters Patent is hereby corrected as shown below:

Column 15, line 38, after "said" delete --,--.

Column 22, line 65, after "set" delete --,--.

Column 28, line 8, change "80" to --86--.

Signed and Sealed this

Eighteenth Day of July, 1995

Attest:

BRUCE LEHMAN

Attesting Officer      Commissioner of Patents and Trademarks